(12) United States Patent
Pan et al.

(10) Patent No.: US 9,187,790 B2
(45) Date of Patent: Nov. 17, 2015

(54) SACCHARIFICATION OF LIGNOCELLULOSIC BIOMASS

(71) Applicant: WISCONSIN ALUMNI RESEARCH FOUNDATION, Madison, WI (US)

(72) Inventors: Xuejun Pan, Fitchburg, WI (US); Li Shuai, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 258 days.

(21) Appl. No.: 13/784,605

(22) Filed: Mar. 4, 2013

(65) Prior Publication Data

US 2013/0252302 A1 Sep. 26, 2013

Related U.S. Application Data

(60) Provisional application No. 61/615,297, filed on Mar. 25, 2012.

(51) Int. Cl.
*C13K 1/02* (2006.01)
*C13K 13/00* (2006.01)
*C12P 7/10* (2006.01)

(52) U.S. Cl.
CPC . *C13K 13/00* (2013.01); *C12P 7/10* (2013.01); *C13K 1/02* (2013.01); *C12P 2203/00* (2013.01); *Y02E 50/16* (2013.01)

(58) Field of Classification Search
CPC ............ C13K 1/02; C13K 13/00; C12P 7/10; C12P 2203/00; Y02E 50/16
See application file for complete search history.

(56) References Cited

U.S. PATENT DOCUMENTS

| | | | |
|---|---|---|---|
| 4,018,620 A | * | 4/1977 | Penque ............................ 127/37 |
| 4,452,640 A | | 6/1984 | Chen et al. |
| 4,637,835 A | | 1/1987 | Nagle |
| 4,681,936 A | | 7/1987 | Pfaff et al. |
| 4,699,124 A | | 10/1987 | Nagle |

(Continued)

OTHER PUBLICATIONS

Binder et al. (2009) "Simple Chemical Transformation of Lignocellulosic Biomass into Furans for Fuels and Chemicals," *J. Am. Chem. Soc.* 131:1979-1985.
Binder et al. (Mar. 9, 2010) "Fermentable sugars by chemical hydrolysis of biomass," *Proc. Natl. Acad. Sci. USA.* 107:4516-4521.

(Continued)

*Primary Examiner* — David M Brunsman
(74) *Attorney, Agent, or Firm* — Lathrop & Gage LLP

(57) ABSTRACT

An efficient process for saccharifying lignocellulosic biomass in concentrated aqueous solutions of certain bromine salts, particularly LiBr and CaBr$_2$. Real lignocellulose biomass, such as corn stover, switchgrass, waste paper, hardwood, and softwood, can be hydrolyzed without the need for any prior pretreatment. Complete saccharification of both cellulose and hemicellulose is achieved within 5-200 min at temperatures ranging from about 100 to about 160° C. Residual lignin is readily separated from product sugars by filtration or centrifugation and can be used to prepare beneficial coproducts. The bromine salt can be recovered and separated from product sugars (predominantly monosaccharides) by any art-known method and in particular solvent extraction, anti-solvent precipitation, ion-exclusion chromatography and/or ion-exchange chromatography can be employed. Hydrolysis product containing sugars can be employed for in fermentation for the production of value added products or useful fuels.

20 Claims, 7 Drawing Sheets

(56) References Cited

U.S. PATENT DOCUMENTS

| | | | |
|---|---|---|---|
| 4,713,118 A * | 12/1987 | Barker et al. | 127/38 |
| 4,787,939 A * | 11/1988 | Barker et al. | 127/37 |
| 5,820,687 A | 10/1998 | Farone et al. | |
| 5,968,362 A | 10/1999 | Russo | |
| 7,452,520 B2 | 11/2008 | Grinbaum et al. | |
| 7,572,925 B2 | 8/2009 | Dumesic et al. | |
| 7,671,246 B2 | 3/2010 | Dumesic et al. | |
| 7,880,049 B2 | 2/2011 | Dumesic et al. | |
| 8,324,376 B2 | 12/2012 | Binder et al. | |
| 8,680,264 B2 | 3/2014 | Binder et al. | |
| 8,722,878 B2 | 5/2014 | Raines et al. | |
| 2008/0033187 A1 | 2/2008 | Zhao et al. | |
| 2009/0124839 A1 | 5/2009 | Dumesic et al. | |
| 2010/0004437 A1 | 1/2010 | Binder et al. | |
| 2010/0170504 A1 | 7/2010 | Zhang | |
| 2013/0305594 A1 | 11/2013 | Shuai et al. | |
| 2014/0090640 A1* | 4/2014 | Shih et al. | 127/29 |
| 2014/0220651 A1 | 8/2014 | Raines et al. | |
| 2014/0235851 A1 | 8/2014 | Binder et al. | |

OTHER PUBLICATIONS

Brendler, E., Fisher, S., and Leipner, H. (2002). 7Li NMR as probe for solvent-cellulose interactions in cellulose dissolution. Cellulose, 8, 283-288.

Fischer, S., H. Leipner, K. Thummler, E. Brendler, J. Peters, (2003) Inorganic molten salts as solvents for cellulose. *Cellulose* 10, 227-236.

Pan et al. (Mar. 31, 2011) "Direct Saccharification and Fractionation of Lignocellulosic Biomass in Concentrated Salt Solution at Moderate Temperature," oral presentation at the 241$^{st}$ American Chemical Society Meeting. Anaheim, California, Mar. 27-31, 2011.

Pan et al. Abstract of Presentation "Direct Saccharification and Fractionation of Lignocellulosic Biomass in Concentrated Salt Solution at Moderate Temperature" submitted to the American Chemical Society on Oct. 18, 2010.

Li Shuai Doctoral Thesis "Transforming Lignocelluloses to Sugars and Liquid Fuels" University of Wisconsin, final oral examination Jun. 2012.

* cited by examiner

SACCHARIFICATION OF LIGNOCELLULOSIC BIOMASS

CROSS-REFERENCE TO RELATED APPLICATIONS

This application claims the benefit of U.S. provisional application 61/615,297, filed Mar. 25, 2012, which is incorporated by reference herein in its entirety.

STATEMENT REGARDING GOVERNMENT SUPPORT

This invention was made with government support under 11-CRHF-0-6055 awarded by the USDA/CSREES. The government has certain rights in the invention.

BACKGROUND OF THE INVENTION

Production of transportation fuels from renewable biomass resources can reduce dependence on traditional fossil fuel, relieve the energy crisis, create new jobs, stimulate local economies, and reduce greenhouse gas emissions. Currently bioethanol is produced from cornstarch or sugarcane. Such processes are not sustainable and are unable to meet the increasing demand for renewable fuels. Sustainable production of biofuel must rely on abundant, inexpensive, and non-food lignocellulosic biomass. A core bottleneck of biomass conversion processes based on a sugar platform is the effective release of sugars from inexpensive, non-food and abundant lignocellulosic biomass at low cost and low energy input [1]. Cellulose in lignocellulosic materials is wrapped by hemicellulose and especially lignin, making cellulose far more difficult to hydrolyze into glucose than starch. In addition cellulose has a crystalline structure and stronger glucosidic bonds than starch (β- vs. α-glucosidic bonds). As a consequence, relatively harsh conditions such as high temperature and more chemicals are needed for hydrolyzing cellulose[2]. Primary methods that have been extensively investigated for saccharification of lignocellulosic materials include concentrated acid, diluted acid, ionic liquid and enzymatic processes.

Concentrated acid saccharification is the most extensively studied cellulose hydrolysis process. This process is conducted at relatively mild temperature and can lead to nearly theoretical yield of sugars. In this process, cellulose in lignocellulosic materials is first swollen at room temperature with concentrated acid (typically sulfuric acid), and then the swollen cellulose is hydrolyzed in diluted acid at elevated temperature (50~120° C.)[3]. However, acid corrosion of equipment and the difficulty in recycling concentrated sulfuric acid have restricted the development of this technology. Although ion exclusion chromatography can be used to separate sugars and sulfuric acid, the method is costly and energy-intensive. In addition, the acid is extensively diluted during the sugar-acid separation, and of the recovered sulfuric acid has to be reconcentrated to 70%~80% prior to reuse.[4]

In order to avoid the use of concentrated acid, a saccharification method using diluted acid at higher temperatures (160~190° C.) was developed. Unfortunately, the dilute acid process only gives a sugar yield of about 50% because of incomplete hydrolysis of cellulose and sugar degradation at high temperature. Additionally, the sugar degradation products, such as furfural, hydroxymethylfurfural (HMF), and levulinic acid, can inhibit the fermentation of the sugars, for example, to produce ethanol. In order to reduce the degradation of sugars, in particular of pentoses, a two-stage process was developed. In a first stage, hemicellulose was first extracted at moderate temperature; and in a second stage, temperature was elevated to hydrolyze cellulose into glucose. Even so, the total yield of sugars was only 60~70%, depending on feedstock and processing conditions[3b, 5]. Further, the need to employ a two-stage process adds to complexity and cost.

In summary, problems encountered with acid processes include low sugar yield due to the incomplete hydrolysis of cellulose and undesirable degradation of the sugars, formation of fermentation inhibitors (furfural, HMF, and levulinic acid etc.), extensively condensed lignin (which limits the coproducts potential of the lignin), equipment corrosion, acid recovery, and wastewater treatment.

The enzymatic saccharification of lignocellulose using cellulose and hemicellulose hydrolytic enzymes is another popular method used to break down cellulose and hemicellulose into monosaccharides. Enzymatic saccharification itself is inexpensive and less hazardous than acid hydrolysis because of the use of mild process conditions (~50° C. and pH 4-5). However, enzymatic saccharification of lignocellulosic biomass is economically less attractive which limits its commercialization. A major obstacle to successful commercialization of enzymatic saccharification is the unavailability of high-activity and low-cost enzymes (both cellulases and hemicellulases). Although significant progress has been made in recent decades in improving enzyme activity and reducing enzyme production cost, enzyme is still a considerable contributor to the high cost of the sugars from lignocellulosic biomass[6]. Additionally, because of the natural recalcitrance of lignocellulosic biomass to the enzymes, enzymatic saccharification of untreated raw biomass is very difficult and very slow. In order to achieve a satisfactory level of cellulose hydrolysis, an energy- and cost-intensive pretreatment operation is required. Such pretreatment functions to remove lignin and/or hemicellulose to expose cellulose. Pretreatment can result in destruction of the physical matrix by mechanically grinding or milling to reduce particle size (and thereby increasing accessible surface area to enzymes), enhancing cellulose hydrolysis by decrystallization and depolymerization, or combinations thereof. Representative pretreatment technologies include, for example, acid treatment (e.g., with diluted acid, concentrated phosphoric acid, etc.); the organosolv process (e.g., U.S. Pat. No. 3,585,104), ammonia fiber expansion (AFEX), treatment with ionic liquid, treatment with alkali, and sulfite processes[7]. However, due to technical and/or economic barriers, none of these technologies has as yet commercially succeeded. In addition, unlike chemical reaction, enzymatic hydrolysis is a time-consuming process and typically takes days to complete. Finally, since high consistency (substrate solid content) hydrolysis is an engineering challenge, enzymatic hydrolysis typically generates a dilute (5-10%, w/w) sugar stream.

Recently, direct hydrolysis of lignocellulosic biomass in ionic liquid has been reported from pure cellulose and real biomass, such as untreated corn stover, wheat and rice straws, and wood powder[8, 9]. The use of ionic liquids can be problematic due to the generally higher cost of these materials and to the complexity that can be encountered in separation of the ionic liquids from products and the recycling of ionic liquids.

U.S. Pat. No. 4,018,620 (Penque) relates to a method of hydrolyzing cellulose to mono saccharides by treating cellulose with aqueous $CaCl_2$ and acid, using 55% calcium chloride in the presence of acid to hydrolyze newsprint (newspaper). An overall saccharification yield of 50% was reported, but cellulose was only hydrolyzed by 20%[10c]. Because of its capability of swelling and dissolving cellulose, $ZnCl_2$ is widely used in cellulose solvent systems[11]. A two-step process was reported to hydrolyze cellulose with $ZnCl_2$, swelling and dissolving cellulose at high $ZnCl_2$ concentration followed by hydrolyzing cellulose to glucose at diluted $ZnCl_2$ in the presence of acid[10d]. It was reported that over 90% of pure cellulose could be saccharified to glucose with the process. However, the process was less effective when applied to real lignocellulosic biomass where an overall saccharification yield of polysaccharides (cellulose and hemicellulose) was 60~70%, but that of cellulose was only 30~50%.

U.S. Pat. Nos. 4,713,118 and 4,787,939 relate to a process for modification, solubilization and/or hydrolysis of a glycosidically linked carbohydrate having reducing groups. The process employs a mixture of water, an inorganic acid and a halide of lithium, magnesium or calcium.

While processes are known in the art for hydrolyzing lignocellulosic materials there is still a significant need in the art for efficient and low-cost processes which provide hydrolysis of lignocellulosic materials, particularly wood-based materials that are hard to hydrolyze, predominantly to monosaccharides, with minimal loss to undesired coproducts and preferably without the need for pretreatment of lignocellulosic materials.

SUMMARY OF THE INVENTION

The present invention provides an efficient process for saccharifying lignocellulosic biomass in concentrated aqueous solutions of certain bromine salts, particularly LiBr. The inventive process hydrolyzes real lignocellulose biomass, such as corn stover, switchgrass, waste paper, hardwood, and softwood, without the need for any prior pretreatment. Complete saccharification of both cellulose and hemicellulose is achieved within 5-200 min at temperatures ranging from about 100 to about 160° C. Residual lignin is readily separated from product sugars by filtration or centrifugation and can be used to prepare beneficial coproducts. The bromine salt, particularly LiBr or $CaBr_2$, can be recovered and separated from product sugars (predominantly monosaccharides) by any art-known method and in particular solvent extraction, anti-solvent precipitation, ion-exclusion chromatography and/or ion-exchange chromatography can be employed.

The process can be applied to lignocellulosic materials without the need for extensive mechanical and/or chemical pretreatment. For example, the process of the invention can be applied to hard and soft wood chips, to sawdust and to wood powders without chemical pretreatment. The process is useful for saccharification of a variety of biomass feedstocks with varying lignin content. The process saccharifies cellulose and hemicellulose of lignocellulosic materials in a single step and provides residual lignin fractionated from cellulose and hemicellulose. The process can provide overall sugar yield of both hexoses and pentoses of greater than 80% and preferably of 90% or more. The process can result in limited sugar degradation and limited formation of fermentation inhibitors, such as furans. The process of the invention can directly saccharify lignocellulose and allow resultant sugars to be separated from residual lignin. Residual lignin can be recovered with high purity and retention of reactivity for modification. The salts employed in the process can be recycled. The process provides improvements in cost and energy efficiency and good scalability. The process of the invention produces a high-concentration (10-100% or preferably 30-100%) sugar solution, which saves cost and energy for concentrating sugar and end products (e.g. ethanol). Product sugars, which are at least predominantly monosaccharides, can be obtained in high purity (e.g., 95% or higher) without significant amounts of sugar degradation products (e.g., furans). Product sugars prepared by the process of this invention can be employed as sugar feedstocks for art-known fermentation and catalytic/thermochemical conversion processes. In specific embodiments, such sugar feedstocks are prepared with sufficiently low levels of sugar degradation product such that inhibition of fermentation is avoided.

In specific embodiments of the invention, biomass loading in the process can be 1% to 100% by weight of lignocellulose to volume of salt solution (i.e. where the ratio of salt solution to lignocellulose ranges from 100:1 to 1:1). In more specific embodiments, biomass loading can be 5%-100% weight to volume (where the ratio of salt solution to lignocellulose ranges from 20:1 to 1:1). In additional specific embodiments, biomass loading can be 10% to 100% weight to volume (where the ratio of salt solution to lignocellulose ranges from 10:1 to 1:1). In additional specific embodiments, biomass loading can be 20% to 100% weight to volume (where the ratio of salt solution to lignocellulose ranges from 5:1 to 1:1).

In specific embodiments, the process of the invention contacts lignocellulosic materials with an aqueous mixture of acid and bromine salt. The bromine salt is present at concentration of 40-80% by weight of the aqueous solution. More specifically, the concentration of bromine salt ranges from 40 to 75% by weight, from 50 to 70% by weight, or from 55 to 65% by weight. In a specific embodiment, the concentration of bromine salt ranges from 57 to 64% by weight. In specific embodiments, the aqueous mixture ranges from 13 to 20 M in bromine ion. In specific embodiments, the aqueous mixture ranges from 16 to 19 M in bromine ion. In specific embodiments, the bromine salt is LiBr, $CaBr_2$, KBr, $AlBr_3$, $MgBr_2$ or NaBr. In more specific embodiments, the bromine salt is LiBr. In other specific embodiments, the bromine salt is $CaBr_2$. In specific embodiments, the bromine salt is LiBr, $CaBr_2$ or a mixture thereof which is present at a total concentration of 52-68% by weight in the reaction medium. In specific embodiments, the bromine salt is LiBr which is present at a concentration of 55-65% by weight in the reaction medium. In specific embodiments, the bromine salt is $CaBr_2$ which is present at a concentration of 55-65% by weight in the reaction medium.

If the lignocellulosic material contains moisture, the amount of salt and the amount of acid in the mixture is adjusted to account for the moisture present. In specific embodiments herein the materials to be solubilized or hydrolyzed are air dried to contain 10% by weight or less moisture.

Acid is an organic or inorganic acid, but is preferably inorganic acid. Acid is present at concentrations less than 1M. In more specific embodiments, acid is present at concentrations of 0.5 M or less, 0.25M or less, 0.1M or less or 0.05M or less. In specific embodiments, the acid is HCl, $H_2SO_4$, $HNO_3$, $H_3PO_4$, or HBr. To lower processing costs, it is preferred to employ HCl or $H_2SO_4$ as the acid. In specific embodiment, acid is added to the hydrolysis reaction based on the amount of biomass (cellulose, lignocellulose, etc.) present and is preferably less than 5% by weight based on biomass to minimize the production of undesired sugar degradation products, such as furans. Higher levels of added acid can be employed to increase the speed of hydrolysis but may generate such degradation products. Such higher levels of acid may be used particularly where the presence of degradation products in the hydrolysis product is not detrimental to further uses of the hydrolysis product. In an embodiment, no acid is added to the reaction which may increase the time required for hydrolysis. In a specific embodiment, acid is added to the hydrolysis reaction based on the amount of biomass (cellulose, lignocellulose, etc.) present and ranges from 1% to 5% by weight based on biomass. In a specific embodiment where the biomass is plant material, such as corn stover, or derived from wood (hardwood or softwood), wherein polysaccharide material can be acetylated, addition of lower levels of acid can be sufficient to achieve fast hydrolysis because of the release of acetic acid on hydrolysis. In specific embodiments wherein biomass contains acetylation, acid levels less that 3% by weight and less than 1% by weight can be employed. In more specific embodiments, the acid is HCl and is added to the hydrolysis reaction based on the amount of biomass (cellulose, lignocellulose, etc.) present and ranges from 1% to 5% by weight based on biomass. In more specific embodiments, the acid is HCl and is added to the hydrolysis reaction based on the amount of biomass (cellulose, lignocellulose, etc.) present and ranges from 2-3.5% by weight based on biomass.

In specific embodiments of the invention, an aqueous solution of 40-70% by weight LiBr and inorganic acid at 1M or less is contacted with lignocellulosic material at temperatures ranging from 100-160° C. to saccharify cellulose and hemicellulose to sugars which are predominantly monosaccharides. In more specific embodiments, the concentration of LiBr is 55-65% by weight and the acid concentration is 0.5M or less. In more specific embodiments, the temperature is 130 to 150° C. and in an additional embodiment the temperature is 135 to 145° C. In additional embodiments, for high sugar yield and low sugar degradation temperatures of 100 to 130° C. and preferably temperatures of about 110° C. can be employed.

In specific embodiments of the invention, an aqueous solution of 53%-68% by weight LiBr and inorganic acid at less than 5% by weigh based on lignocellulosic material is contacted with the lignocellulosic material at temperatures ranging from 105-130° C. to saccharify cellulose and hemicellulose to sugars which are predominantly monosaccharides. In more specific embodiments, the concentration of LiBr is 56-64% by weight and the acid concentration is 2-3.5% by weight based on biomass present.

In specific embodiments, biomass hydrolysis reactions are run for 15 to 60 minutes at temperatures ranging from 105-130° C. and achieve 80% or higher conversion of polysaccharides (cellulose and hemicellulose) present. In specific embodiments, such biomass hydrolysis reactions are run employing LiBr or $CaBr_2$ or mixtures thereof at salt ranging from 55-65% (w/v). In specific embodiments, such biomass hydrolysis reactions employ HCl at less than 5% by weight based on biomass added. In specific embodiments, biomass hydrolysis reaction of the invention are run for 15 to 60 minutes at temperatures ranging from 105-130° C. and achieve 90% or higher conversion of polysaccharides (cellulose and hemicellulose) present. In specific embodiments, biomass hydrolysis reaction of the invention are run for 15 to 60 minutes at temperatures ranging from 105-130° C., achieve 90% or higher conversion of polysaccharides (cellulose and hemicellulose) present and generate 5% or less total HMF and furfural based on available hexoses and pentoses in original feedstock.

The method of the invention can be used with lignocellulosic materials containing up to about 30% by weight lignin. In specific embodiments, the process is useful for solubilizing and hydrolysis of lignocellulosic materials having from 0.5 to 10% or higher by weight lignin. In specific embodiments, the process of the invention is useful for hydrolysis of lignocellulosic materials having 15% or higher by weight lignin. More specifically, the process of the invention is useful for lignocellulosic materials having 18% or higher by weight lignin. As has been noted elsewhere herein, the method of the invention can be applied to pretreated lignocellulosic materials in which the lignin matrix is at least partially disrupted. Additionally, the method herein can be applied to cellulose, hemicellulose, starch and other carbohydrate materials derived from biomass.

While the process of the invention is preferably applied to lignocellulosic materials, the process can in addition be applied to cellulose, hemicellulose, starch, as well as other polysaccharides and mixtures thereof.

In another aspect, the invention provides a method for solubilizing and optionally partially hydrolyzing lignocellulosic materials that comprises contacting the lignocellulosic materials from pure cellulose to high-lignin lignocellulosic biomass with an aqueous solution containing a bromine salt at a concentration of 40-70% by weight. Solubilization can be conducted at temperatures ranging from 100 to 160° C., but lower temperatures of 100-140° C. are preferably for solubilization. In this aspect of the invention no organic or inorganic acid is added to the salt solution. The salt solution employed is as described herein above for saccharification of lignocellulosic material except that no organic or inorganic acid is added to the salt solution. This process can be used to release polymeric and oligomeric saccharides from the lignocellulosic materials and provide residual materials enhanced in lignin content.

Saccharides released from lignocellulosic material by this process can comprise monosaccharides, disaccharides, oligomeric saccharides, and polymeric saccharides. Saccharides released by this process can be further hydrolyzed to monosaccharides and can be directly employed as feedstocks for other processes, such as fermentation processes. Dissolved polysaccharides (cellulose) can be used to produce regenerated cellulose products (e.g. fibers or films). Residual lignin produced by this process can be employed for the production of coproducts as is known in the art. In a specific embodiment, saccharides released by this process can be hydrolyzed by addition of dilute acid (e.g., 1-5% concentration) with heating at temperatures ranging from 100-160° C. In a specific embodiment, saccharides released by this process can be hydrolyzed by addition of dilute acid (e.g., 1-5% concentration) with heating at temperatures ranging from 100-130° C. In another specific embodiment, saccharides released by this process can be hydrolyzed by addition of dilute acid (e.g., 1-5% concentration) with heating at elevated pressure, for example heating at temperatures ranging from 50-120° C. at up to 2 atm. In another embodiment, saccharides released by this process can be hydrolyzed by addition of dilute acid (e.g., 1-5% concentration) with heating at elevated pressure, for example by subjecting the mixture to conventional autoclaving. In another specific embodiment, saccharides released by this process can be hydrolyzed enzymatically as is known in the art.

In specific embodiments of this aspect of the invention, the bromine salt is LiBr or $CaBr_2$ and the concentration of the salt ranges from 55-65% by weight. In specific embodiments, the process is conducted at temperatures ranging from 100-160° C. In other embodiments, the process is conducted at temperatures ranging from 100-130° C. In yet other embodiments, the process is conducted at a temperature of about 110° C. In specific embodiments, the ratio of salt solution to lignocellulosic material is 100–1 to 1. In other specific embodiments, the ratio of salt solution to lignocellulosic material is 10 to 1. In other specific embodiments, the ratio of salt solution to lignocellulosic material is 1 to 1.

The invention is also directed to methods for separating concentrated salts employed for solubilization and hydrolysis of cellulose, hemicellulose, other polysaccharides and lignocellulosic material from resultant sugars. The methods of this invention result in salt-sugar product mixtures. These product mixtures can contain varying amounts of water. Dependent upon the separation method employed, it can be beneficial to remove water from the salt-sugar product mixtures prior to separation. Removal of water may result in the formation of salt-sugar syrups.

In a specific embodiment, steps of ion exclusion chromatography, steps of ion exchange chromatography and/or precipitation methods can be used to at least partially separate salt from sugar in salt-sugar product mixtures. In a specific embodiment, sequential steps of anion and cation exchange can be employed to remove salt from sugar solutions.

In a specific embodiment, sugars can be extracted from salt-sugar product mixtures using boronic acid extraction to provide at least partial separation of sugars and salt. This type of extraction may employ a single extraction step or multiple extraction steps. In a specific embodiment, the salt-sugar product mixture is extracted with an organic solvent phase containing the boronic acid and a lipophilic quaternary ammonium salt. In a specific embodiment, the boronic acid is naphthalene-2-boronic acid. In a specific embodiment, the organic solvent phase is a mixture of hexane with octanol or higher alcohol. Additional salt can be removed from sugar extracts employing steps of ion exchange chromatography (including sequential steps of anion and cation exchange) and/or precipitation. A preferred method of precipitation is precipitation employing a carbonate salt, particularly sodium carbonate.

In as specific embodiment, the salt-sugar product mixtures can be extracted with an organic solvent phase in which sugars are not soluble to remove salt. In specific embodiments, the organic solvent phase is an alkyl alcohol, such as butanol (e.g., n-butanol), a ketone, such as methyl isobutyl ketone, ether or an ester, mixtures thereof or mixtures of the alcohol, ketone, ether or ester with a non-polar or low polarity hydrocarbon, such as a alkane, alkene, aromatic compounds or mixture thereof. In a specific embodiment, the organic phase is a mixture of alcohol and alkane, such as butanol/hexane mixtures. Agents which selectively complex cations or anions of the salt can also be added to the organic phase to facilitate removal of salt. For example, tributyl phosphine or crown ethers can be employed to extract lithium.

Residual salt can removed from sugars employing steps of ion exchange chromatography (including sequential steps of anion and cation exchange) and/or precipitation. A preferred method of precipitation is precipitation employing a carbonate salt, particularly sodium carbonate.

In specific embodiments, the salt-sugar product mixture is separated by one or more methods herein such that the salt remaining in the sugar product is less than 10% by weight.

In other embodiments, the salt-sugar product mixture is separated by one or more methods herein such that the salt remaining in the sugar product is less than 1% by weight.

The methods of this invention can be employed to prepare sugar product of varied concentrations ranging from dilute solutions to dry solid sugar and with varied residual salt ranging from substantially salt-free (less than 0.1% by weight) to 10% by weight (or higher if the higher salt content is tolerated in the application to which the sugar product is applied.

Other aspects and embodiments of the invention will be apparent to one or ordinary skill in the art on consideration of the following non-limiting description and examples.

DETAILED DESCRIPTION OF THE INVENTION

The present invention relates to the treatment of lignocellulosic materials with concentrated aqueous bromine salt solutions to solubilize and release saccharides from these materials and generate separated lignin. In one aspect, the treatment releases saccharides predominantly as oligomeric saccharides which can be employed as fermentation feedstock, feedstock for additional enzymatic or chemical hydrolysis to monosaccharides or feedstock for conversion to useful products such as furans. Fermentation of feedstocks containing oligomeric saccharides or monosaccharides can produce fuel, such as ethanol or a variety of value-added fermentation products. In another aspect, dilute acid is added to the salt solution and treatment of lignocellulosic materials results in hydrolysis and generation of saccharides predominantly as monosaccharides along with separated residual lignin.

Lignocellulosic materials include, among others, plant materials, crops, energy crops (crops intended for conversion to fuel such as switchgrass, *Miscanthus giganteus*, etc.), agricultural residue (e.g., corn stover, sugar cane bagasse), paper waste (e.g., newsprint) and hard or soft wood or wood residue (wood chips, wood powder saw dust). Lignocellulosic materials can be pre-treated by physical methods, such as grinding, chopping or mashing. While not required, lignocellulosic material may be pre-treated by various chemical or biological methods known in the art. Wood materials are preferably chopped or grounds to form chips or powders. It will be appreciated that lignocellulosic materials may include cellulose, hemicellulose and other biomass carbohydrates free from the lignin matrix. Lignocellulosic materials can contain varying amounts of moisture. Fresh lignocellulosic material can contain up to about 50% by weight water. The amount of slat and acid added to reactions herein is adjusted to account for the moisture content of the material to be solubilized or hydrolyzed to avoid unintended significant dilution. In examples herein, lignocellulosic materials are air dried to have a moisture content of 10% by weight or less. Various methods are known for drying lignocellulosic material all of which can be applied is desired. It will be appreciated that methods which expend less energy for any drying will be more preferred.

The following detailed description is largely directed to the use of LiBr as an exemplary bromine salt. LiBr is a preferred bromine salt but the processes of this invention can be practiced with other bromine salts, including those of alkali metals, alkaline earth metals and certain other metals. The following description generally applies to the use of other bromine salts. Bromine salts that are useful in the invention include, among others, LiBr, $CaBr_2$, KBr, $MgBr_2$, $AlBr_3$, $ZnBr_2$, NaBr and mixtures thereof.

Figure 1:
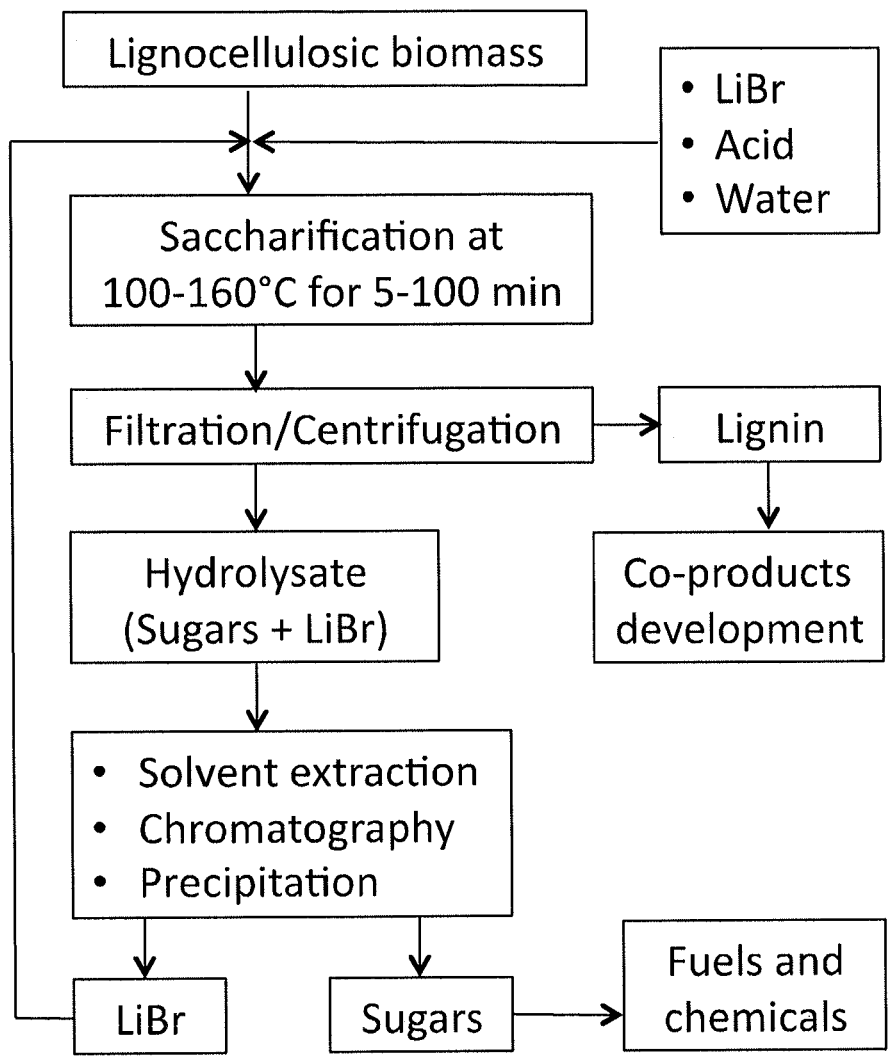
FIG. 1 is a schematic flowchart of direct saccharification of lignocellulosic biomass in concentrated LiBr.

As schematically shown in FIG. 1, real biomass (such as, corn stover, switchgrass, hardwood, and softwood) is mixed with LiBr, a small amount of acid, and water at a desired LiBr concentration (e.g., 40-70%). The mixture is heated at elevated temperature (for example, 100-160° C., more preferably 110-130° C.) for typically several minutes to several hours (dependent on acid concentration, salt concentration, biomass species and particle size) with stirring. Both cellulose and hemicellulose of the biomass are completely hydrolyzed (saccharified), while lignin (up to 30% of the biomass) remains as insoluble residue.

By filtration or centrifugation, lignin is separated from the solution of sugars and LiBr. The sugars from cellulose and hemicellulose and LiBr can be further separated with ion exchange, extraction, or crystallization methods based on their difference in ionization and solubility in water and organic solvents. The recovered LiBr can be reused in the process, and the sugars can be converted into biofuels and chemicals by biological or chemical approaches.

The fast chemical saccharification method as illustrated in FIG. 1 is able to simultaneously hydrolyze cellulose and hemicellulose of the biomass without the need for extensive size reduction of the biomass or any chemical pretreatment of the biomass. The process can produce a concentrated sugar solution (>30%, w/w) and even dry solid sugars at high yield with limited degradation of sugars to furans (furfural and hydroxymethylfurfural). Sugars produced are predominantly monosaccharides. In addition, the process can directly handle small size wood chips without extensive size reduction and any pretreatment, which significantly simplifies operation and reduces processing cost and energy consumption.

Figure 2:
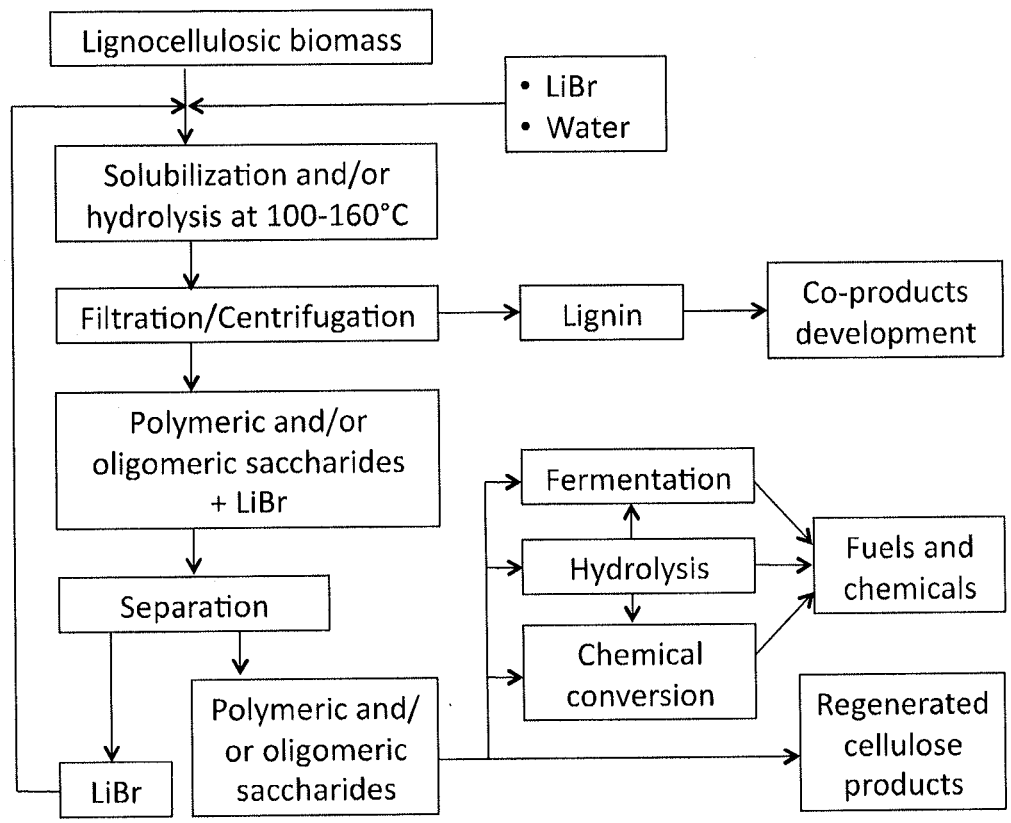
FIG. 2 is a schematic flowchart of solubilization and hydrolysis of lignocellulosic biomass in concentrated LiBr.

FIG. 2 illustrates an exemplary process of another aspect of the invention. As schematically shown in FIG. 2, real biomass (such as, cellulose, corn stover, switchgrass, hardwood, and softwood) is mixed with LiBr and water at a desired LiBr concentration (e.g., 40-70%). The mixture is heated at elevated temperature (for example, 100-160° C.) for typically several minutes to several hours (dependent on salt concentration, biomass species and particle size) with stirring. The biomass is solubilized and saccharides are released mainly in the form of oligosaccharides and/or polysaccharides and lignin remains as an insoluble residue which can be separated and employed for any art-recognized application. Recovered salt can be reused in the process, and the saccharides can be directly converted into biofuels and chemicals by biological or chemical approaches or can be initially hydrolyzed to monosaccharides (chemically and/or biologically) and thereafter converted to biofuels and/or chemicals, again chemically or biologically. As in the process of FIG. 1, small size wood chips can be processed without extensive size reduction and any pretreatment.

Without wishing to be bound by any particular mechanism, the following discussion of the possible mechanism of solubilization and hydrolysis of the present invention is provided. In dilute LiBr solution, both $Br^-$ and $Li^+$ are solvated through water coordination. However, since water is in deficit in concentrated LiBr solution, dependent on the concentration of LiBr, a portion of $Br^-$ and $Li^+$ are "naked" or "unsolvated" with water. The non-solvated $Br^-$ and $Li^+$ interact with hydroxyl groups of cellulose to form $Li^+.O$ and $Br^-.H$ bonds, which disrupts the intermolecular and intramolecular hydrogen bonds of cellulose and therefore enhances the dissolution and hydrolysis of cellulose. Presumably LiBr enhances the hydrolysis of cellulose and hemicellulose in three ways. First, in concentrated LiBr solution, "naked" or "unsolvated" $Br^-$ and $Li^+$ tend to interact with hydroxyl groups of cellulose through hydrogen bonding. Mechanism will be further discussed below. In addition, the bulky bromide anion as a spacer is able to create more room between cellulose molecules to facilitate the penetration of solvent and the swelling/dissolution of cellulose. Second, acid ($H^+$) added in concentrated LiBr solution is not solvated and therefore is more active than solvated protons, which enhances the acidic hydrolysis of glucosidic bonds of cellulose. Third, $Li^+$ as a Lewis acid itself may also catalyze cleavage of glucosidic linkages. As will be discussed in Example 2, LiBr itself without addition of acid is capable of hydrolyzing cellulose and hemicellulose; though the reaction is slow and hydrolysis is incomplete (the majority of the hydrolysis products are in form of oligomeric sugars).

Scheme 1. Hydrolysis pathway of lignocellulose in concentrated LiBr solution

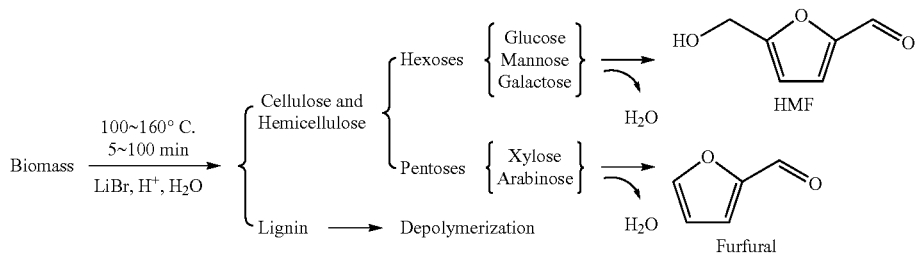

The proposed reaction pathways for the hydrolysis of lignocellulose in concentrated LiBr solution are summarized in Scheme 1. Cellulose and hemicellulose in the biomass are hydrolyzed with acid and LiBr as catalysts into corresponding monomeric sugars, including glucose, xylose, mannose, arabinose, and galactose, dependent on the species of the biomass. A portion of the sugars may be in the form of oligomers due to incomplete hydrolysis. A small amount of the monomeric sugars may be further dehydrated into furfural (from pentoses) and hydroxymethylfurfural (HMF, from hexoses), when the reaction conditions are severe (higher temperature and acid dosage). Lignin of the biomass may be partial depolymerization through cleavage of ether linkages catalyzed by bromide anion ($Br^-$). The lignin will, however, remain in an insoluble form, which allows easy separation of lignin from the sugars and LiBr by filtration or centrifugation. Residual lignin from the processes herein can be employed as is known in the art for production of co-products.

Separation of Salt from Salt-Sugar Products of the Invention

The methods of this invention can be employed to prepare sugar product of varied concentrations ranging from dilute solutions to dry solid sugar and with varied residual salt ranging from substantially salt-free (less than 0.1% by weight) to 10% by weight (or higher if the higher salt content is tolerated in the application to which the sugar product is applied). The amount of salt in the sugar product can be decreased, if desired, by one or more separation methods described herein or by any other methods that are known to one of ordinary skill in the art.

The methods of this invention result in salt-sugar product mixtures. These product mixtures can contain varying amounts of water. Dependent upon the separation method employed, it can be beneficial to remove water from the salt-sugar product mixtures prior to separation. Removal of water may result in the formation of salt-sugar syrups. Water can be removed from product mixtures by any methods known in the art, for example by vaporization or other drying method. Less energy intensive drying methods are preferred.

As illustrated in the Examples herein, ion exclusion chromatography, steps of ion exchange chromatography and/or crystallization or precipitation methods can be used to at least partially separate salt from sugar in salt-sugar product mixtures. In a specific embodiment, sequential steps of anion and cation exchange can be employed to remove salt from sugar solutions. It will be appreciated by one of ordinary skill in the art that such separation methods are amenable to application of large scale industrial processing to decrease the cost and increase the efficiency of separation. One of ordinary skill in the art is aware of industrial methods for practicing the separation methods as exemplified herein.

Extraction methods can be employed to separate salt from salt-sugar products of this invention. In a specific embodiment, sugars can be extracted from salt-sugar product mixtures using boronic acid extraction to provide at least partial separation of sugars and salt. This type of extraction may employ a single extraction step or multiple extraction steps. In a specific embodiment, the salt-sugar product mixture is extracted with an organic solvent phase containing the boronic acid and a lipophilic quaternary ammonium salt. In a specific embodiment, the boronic acid is naphthalene-2-boronic acid. In a specific embodiment, the organic solvent phase is a mixture of hexane with octanol or higher alcohol. Additional salt can be removed from sugar extracts employing steps of ion exchange chromatography (including sequential steps of anion and cation exchange) and/or precipitation. A preferred method of precipitation is precipitation employing a carbonate salt, particularly sodium carbonate. The extraction can be practiced employing any known method for extraction on an industrial scale. One of ordinary skill in the art can select appropriate extraction equipment to accomplish the extractions as exemplified herein.

In as specific embodiment, the salt-sugar product mixtures can be extracted with an organic solvent phase in which sugars are not soluble to remove salt. In specific embodiments, the organic solvent phase is an alkyl alcohol, such as butanol (e.g., n-butanol), a ketone, such as methyl isobutyl ketone, ether or an ester, mixtures thereof or mixtures of the alcohol, ketone, ether or ester with a non-polar or low polarity hydrocarbon, such as a alkane, alkene, aromatic compounds or mixture thereof. In a specific embodiment, the organic phase is a mixture of alcohol and alkane, such as butanol/hexane mixtures. Agents which complex cations or anions of the salt can also be added to the organic phase to facilitate removal of salt. For example, tributyl phosphine or crown ethers can be employed to extract lithium. Additional useful complexing agents are known to one of ordinary skill in the art. The extraction can be practiced employing any known method for extraction on an industrial scale. One of ordinary skill in the art can select appropriate extraction equipment to accomplish the extractions as exemplified herein.

In a specific embodiment, residual salt can removed from sugars employing steps of ion exchange chromatography (including sequential steps of anion and cation exchange) and/or precipitation or crystallization. A preferred method of precipitation is precipitation employing a carbonate salt, particularly sodium carbonate. Ion exchange chromatography can be practiced employing any known method on an industrial scale. One of ordinary skill in the art can select appropriate ion exchange columns, pumps and related equipment to accomplish the ion exchange separation as exemplified herein. Precipitation and or crystallization methods can be practiced employing any known method on an industrial scale. One of ordinary skill in the art can select appropriate equipment to accomplish precipitation and crystallization as exemplified herein.

In a specific embodiment, residual salt can removed from sugars employing steps of ion exclusion chromatography (including sequential steps of anion and cation exchange) and/or precipitation. Ion exclusion chromatography can be practiced employing any known method on an industrial scale. One of ordinary skill in the art can select appropriate ion exclusion columns and materials, pumps and related equipment to accomplish the ion exchange separation as exemplified herein.

Methods employing extraction are preferred for separation salt form salt-sugar products of this invention. One of ordinary skill in the art will recognize that liquid-liquid extraction is a mature unit operation in chemical engineering which can be operated in batch or continuous mode. To improve extraction efficiency, for example, multiple-stage countercurrent continuous processes can be used. More detail of liquid-liquid extraction methods and equipment is provided in Perry's Chemical Engineers' Handbook (Eighth Addition, 2008) Section 15 (McGraw-Hill Publishers, New York, N.Y.); Muller et al. (2002) Liquid-Liquid Extraction in Ullmann's Encyclopedia of Industrial Chemistry, Wiley-VCH.

In specific embodiments, the salt-sugar product mixture is separated by one or more methods herein such that the salt remaining in the sugar product is less than 10% by weight.

In other embodiments, the salt-sugar product mixture is separated by one or more methods herein such that the salt remaining in the sugar product is less than 1% by weight.

When a Markush group or other grouping is used herein, all individual members of the group and all combinations and subcombinations possible of the members of the groups therein are intended to be individually included in the disclosure. Every formulation or combination of components described or exemplified herein can be used to practice the invention, unless otherwise stated.

Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that separation methods, lignocellulosic materials, biomass carbohydrates, reagents, purification methods, analytical methods, and reaction conditions other than those specifically exemplified herein can be employed in the practice of the invention without resort to undue experimentation. All art-known functional equivalents, of any such methods, materials and conditions are intended to be included in this invention.

Whenever a range is given in the specification, for example, a temperature range, a time range, or a composition range, all intermediate ranges and subranges thereof, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the broad term "comprising", particularly in a description of components of a composition or in a description of elements of a device, is intended to encompass and describe the terms "consisting essentially of" or "consisting of".

Although the description herein contains many specific details, these should not be construed as limiting the scope of the invention, but as merely providing illustrations of some of the embodiments of the invention. In particular, the examples provided herein are not intended to be limiting.

Each reference cited herein is incorporated by reference herein in its entirety. In the case of any inconsistency between the content of a cited reference and the disclosure herein, the disclosure of this specification is to be given priority. Some references cited herein are incorporated by reference to provide details concerning prior art processes, biomass sources, methods of pretreatment of biomass, additional methods of analysis and additional uses of treated lignin of this invention.

THE EXAMPLES

Example 1

Materials and Methods

Air-dried lignocellulosic materials, ground using a Wiley mill to pass a 40-mesh screen, were used in the present study. Chemical composition of different types of lignocellulosic biomass is presented in Table 1. All the chemical reagents and solvents used in this study were purchased from Fisher Scientific or sigma-Aldrich and used as received.

TABLE 1

| Composition analysis of different feedstock | | | | | | |
|---|---|---|---|---|---|---|
| Composition, % | Spruce | Corn Stover | Poplar | Switch grass | Newspaper | Printpaper |
| Moisture | 10.00 | 4.50 | 9.56 | 9.86 | ND | ND |
| Extractive | 5.00 | 15.50 | 6.32 | 16.58 | ND | ND |
| Saccharide Arabinose | 0.98 | 2.71 | 0.29 | 1.93 | 0.35 | 0.19 |
| Galactose | 2.34 | 1.05 | 0.53 | 0.71 | 0.40 | 0.08 |
| Glucose | 42.03 | 35.28 | 43.45 | 29.66 | 63.20 | 71.28 |
| Xylose | 5.18 | 18.40 | 13.41 | 18.01 | 12.13 | 14.74 |
| Mannose | 10.18 | 0 | 2.34 | 0.33 | 4.86 | 3.41 |
| Total lignin | 26.88 | 16.78 | 19.42 | 15.51 | 13.08 | 3.22 |

Note:
ND, not determined.

Quantification of Sugars

Sugar analysis was conducted using a Dionex High Performance Ion Chromatography (HPIC) system (ICS-3000) equipped with integrated amperometric detector and Carbopac™ PA1 guard and analytical columns at 20° C. Eluent was provided at a rate of 0.7 mL/min, according to the following gradient: 0~25 min, 100% water; 25.1~30 min, 30% water and 70% 0.1 M NaOH; 30.1~35 min, 100% water. To provide a stable baseline and detector sensitivity, 0.5 M NaOH at a rate of 0.3 mL/min was used as post-column eluent.

Quantification of Sugar Degradation Products

5-Hydroxylmethylfurural (HMF) and furfural were analyzed using the Dionex ICS-3000 equipped with a Supelcogel C-610H column at temperature 30° C. and UV detector at 210 nm. Eluent was 0.1% phosphoric acid at a rate of 0.7 mL/min.

Quantification of LiBr

Lithium bromide was quantified by titration according to the Mohr method (http://www.titrations.info/precipitation-titration-argentometry-chlorides-Mohr). Content of Br⁻ and Cl⁻ was determined by titration with $AgNO_3$ with $KCrO_4$ as indicator. The reactions in the titration are shown below.

$$Br^- + Ag^+ \rightarrow AgBr \text{(yellow precipitate)}$$

$$Cl^- + Ag^+ \rightarrow AgCl \text{(white precipitate)}$$

$$Ag^+ + CrO_4^- \rightarrow AgCrO_4 \text{(red precipitate)}$$

Example 2

Solubilization of Cellulose in Concentrated LiBr Solution

Dissolution in 61.7% LiBr solution (equivalent to LiBr.3H₂O) of different cellulose samples, including microcrystalline cellulose (MC, Avicel® FMC Biopolymer), dissolving pulp (DP, bleached pre-hydrolyzed kraft pulp of hardwood), and cellulose filter paper (FP, Whatman, UK), was investigated. The results are summarized in Table 2. It is clear that 61.7% LiBr solution is able to swell and dissolve cellulose.

TABLE 2

Dissolution of cellulose in aqueous LiBr solution (61.7%)

| Cellulose concentration | Temp. (°C.) | Time | Observation | Molecular weight Before dissolution | Molecular weight After dissolution |
|---|---|---|---|---|---|
| 2% MC | 100 | 1 h | Swelled and dispersed | $2.63 \times 10^4$ | |
| 4% MC | 100 | 2 h | Swelled and dispersed | $2.63 \times 10^4$ | |
| 2% MC | 120 | 5 min | Dissolved | $2.63 \times 10^4$ | $2.6 \times 10^4$ |
| 4% MC | 120 | 8 min | Dissolved | $2.63 \times 10^4$ | $2.61 \times 10^4$ |
| 6% MC | 120 | 15 min | Dissolved | $2.63 \times 10^4$ | $2.56 \times 10^4$ |
| 2% MC | 140 | 3 min | Dissolved | $2.63 \times 10^4$ | $2.52 \times 10^4$ |
| 4% MC | 140 | 5 min | Dissolved | $2.63 \times 10^4$ | $2.52 \times 10^4$ |
| 6% MC | 140 | 8 min | Dissolved | $2.63 \times 10^4$ | $2.50 \times 10^4$ |
| 8% MC | 140 | 10 min | Dissolved | $2.63 \times 10^4$ | $2.41 \times 10^4$ |
| 1% DP | 120 | 4.5 h | Swelled and dispersed | $2.49 \times 10^5$ | |
| 1% DP | 140 | 1 h | Dissolved | $2.49 \times 10^5$ | |
| 1% FP | 140 | 7 min | Dissolved | $5.09 \times 10^5$ | |

At the lower temperature of 100° C., the concentrated LiBr only swells, and does not dissolve cellulose. By increasing the temperature to 120° C. or higher (e.g., 120-140° C.), cellulose can be completely dissolved in concentrated LiBr. Increasing cellulose loading (concentration) generally required longer times to dissolve cellulose. Dissolution time is dependent on the cellulose sources. Dissolving pulp required generally higher temperatures and times to dissolve in concentrated LiBr than microcrystalline cellulose or cellulose filter paper. This is presumed to be due to the difference of the cellulose samples in molecular weight, crystallinity, fiber morphology, and impurity content.

It was found in microcrystalline cellulose samples that after dissolution, the molecular weight of cellulose had decreased slightly, indicating that some degree of cellulose depolymerization (hydrolysis) took place during dissolution.

It is believed that the ability of concentrated LiBr to swell and dissolve cellulose is important for rapid and complete saccharification of lignocellulose in concentrated LiBr solution, making cellulose therein more accessible to hydrolytic agents.

Example 3

Enhanced Acidity in LiBr Solution

Hammett acidity of 0.5% $H_2SO_4$ was determined in water and LiBr solution at varied LiBr concentrations.[18] The results are summarized in Table 3. At the same acid loading, the acidity was measured to be significantly higher in LiBr solution than in water (a more negative value means higher Hammett acidity). In addition, Hammett acidity increased with LiBr concentration. Enhanced acidity in bromine salt solution is believed to be one of the reasons why lignocellulosic biomass is saccharified faster in concentrated LiBr solution than in water or diluted LiBr solution.

TABLE 3

Hammett acidity of 0.5% $H_2SO_4$ in water and LiBr solution

| | Hammett acidity | |
|---|---|---|
| | 4-chloro-2-nitroaniline method | 2-nitroaniline method |
| 55% LiBr + 0.5% $H_2SO_4$ | −2.85 | −2.22 |
| 49% LiBr + 0.5% $H_2SO_4$ | −2.18 | −1.85 |
| 45% LiBr + 0.5% H2SO4 | −1.61 | −1.40 |

TABLE 3-continued

Hammett acidity of 0.5% $H_2SO_4$ in water and LiBr solution

| | Hammett acidity | |
|---|---|---|
| | 4-chloro-2-nitroaniline method | 2-nitroaniline method |
| 41% LiBr + 0.5% $H_2SO_4$ | −1.23 | −1.05 |
| $H_2O$ + 0.5% $H_2SO_4$ | 0.04 | 0.51 |

Example 4

Solubilization and Hydrolysis of Biomass in Concentrated LiBr Solution without Addition of Acid Spruce powder was liquefied/hydrolyzed in concentrated LiBr solution to release saccharides (both oligosaccharides and monosaccharides) at temperature (120-160° C.). Spruce powder could be liquefied in less than 30 min under selected conditions. The effect of temperature and LiBr concentration on the hydrolysis of spruce in LiBr solution is summarized in FIG. 3. At 120° C., no glucose or glucose degradation product (HMF) was detected, and only particle size reduction was observed, indicating that the dissolution/hydrolysis of cellulose was limited at low temperature. At 140° C., spruce powder was rapidly liquefied in 10 to 20 min, depending on the concentration of LiBr solution. With the increase in LiBr concentration, dissolution/hydrolysis of spruce powder was enhanced, in particular when LiBr concentration is higher than 55% (w/w). This is probably attributed to the formation of "unsolvated" $Li^+$ and "naked" $Br^-$, as mentioned above and will be discussed below, which promotes the dissolution of cellulose through disrupting hydrogen bonds in cellulose crystal. At 60% (w/w) concentration of LiBr, cellulose in the spruce powder was completely dissolved/hydrolyzed, generating 85% soluble saccharides (composition analysis shown in Tables 5 and 6) and 15% HMF from dehydration of glucose. Further increasing LiBr concentration led to a decrease in cellulose dissolution/hydrolysis. This is believed due to the insufficiency of the water needed for cellulose hydrolysis.

Pure cellulose such as microcrystalline cellulose (e.g., Avicel® microcrystalline cellulose, FMC Biopolymer) and dissolving pulp (bleached wood pulp typically having >95% cellulose) were tested as well for solubilization and hydrolysis in concentrated LiBr. The results showed that the pure cellulose was dissolved faster (5-30 min) at the same conditions (60% LiBr solution at 140° C.) than real biomass, because of the absence of blocking from hemicellulose and lignin. It was found that the molecular weight of cellulose slightly decreased during the solubilization in LiBr, indicating that cellulose hydrolysis occurred during the solubilization. Increasing temperature or extending time could make the cellulose significantly hydrolyzed (depolymerized).

In light of the excellent dissolution/hydrolysis ability of 60% LiBr solution, hydrolysis of different feedstocks in 60% solution at 140° C. was investigated. Table 4 shows the comparison of theoretical lignin content and the amount of residues after hydrolysis. The results indicated that almost all carbohydrates were dissolved. Tables 5 and 6 show the carbohydrate composition in the hydrolysates before and after autoclaving at 120° C. for one hour, respectively. It is believed that autoclaving at 120° C. can completely hydrolyze oligosaccharides into monosaccharides. Comparing the results in Tables 5 and 6, one can find that autoclaved hydrolysates contained much more monosaccharides than original hydrolysates, implying that most of carbohydrates dissolved from lignocelluloses in concentrated LiBr solution without acid existed in the form of water-soluble oligosaccharides.

TABLE 4

LiBr-hydrolysis of various types of feedstock

| Feedstock | Theoretical lignin content, % | Residue left, % |
|---|---|---|
| Switch grass | 16 | 21 |
| Spruce | 27 | 25.7 |
| Poplar | 20 | 22 |
| Corn stover | 17 | 22.5 |

Note:
reaction condition: 1 ml $H_2O$, 1500 mg LiBr, 100 mg lignocelluloses powder, 140° C., and 2 h.

TABLE 5

Monosaccharides in the hydrolysates from LiBr hydrolysis of different feedstocks without acid

| | Corn stover | Switchgrass | Poplar | Spruce |
|---|---|---|---|---|
| Arabinose | 0.66 | 0.86 | 0.25 | 0.59 |
| Galactose | 0.39 | 0.55 | 0.39 | 1.31 |
| Glucose | 2.079 | 5.11 | 8.08 | 9.00 |
| Xylose | 7.059 | 9.42 | 7.37 | 2.00 |
| Mannose | 0 | 0 | 2.80 | 6.04 |

Note:
reaction condition: 1 mL $H_2O$, 1500 mg LiBr, 100 mg lignocelluloses powder, 140° C., and 2 h.

TABLE 6

Monosaccharides in hydrolysate from LiBr hydrolysis of different feedstocks after autoclaving at 120° C. for one hour

| % | Corn stover | Switchgrass | Poplar | Spruce |
|---|---|---|---|---|
| Arabinose | 0.73 | 1.07 | 0.21 | 0.67 |
| Galactose | 0.55 | 1.09 | 0.57 | 2.70 |
| Glucose | 30.84 | 26.43 | 39.53 | 40.32 |
| Xylose | 16.26 | 14.06 | 9.63 | 3.34 |
| Mannose | 0 | 0 | 4.72 | 7.56 |

Note:
autoclave procedure: 1 mL hydrolysate was mixed with 1 mL 6% sulfuric acid solution into 2 mL hydrolysate with 3% acid concentration. This solution was autoclaved at 120° C. for 1 hour to hydrolyze oligosaccharides into monosaccharides.

Example 5

Saccharification of Lignocellulosic Biomass in Concentrated LiBr Solution with Addition of Acid The experimental results in Example 4 indicated that concentrated LiBr is capable of dissolving and hydrolyzing polysaccharides in lignocellulosic biomass, but the hydrolysis is incomplete and slow, and that most of hydrolysis products were in form of oligosaccharides. To accelerate the hydrolysis of polysaccharides, acid was added in the LiBr solution. The process conditions were further optimized within the range of LiBr concentration 44-60% (w/w), temperature 110-160° C., acid loading 1-10% on spruce powder, and reaction time 5-60 min, as summarized in Table 7.

Example 6

Effect of LiBr Concentration

Figure 3:
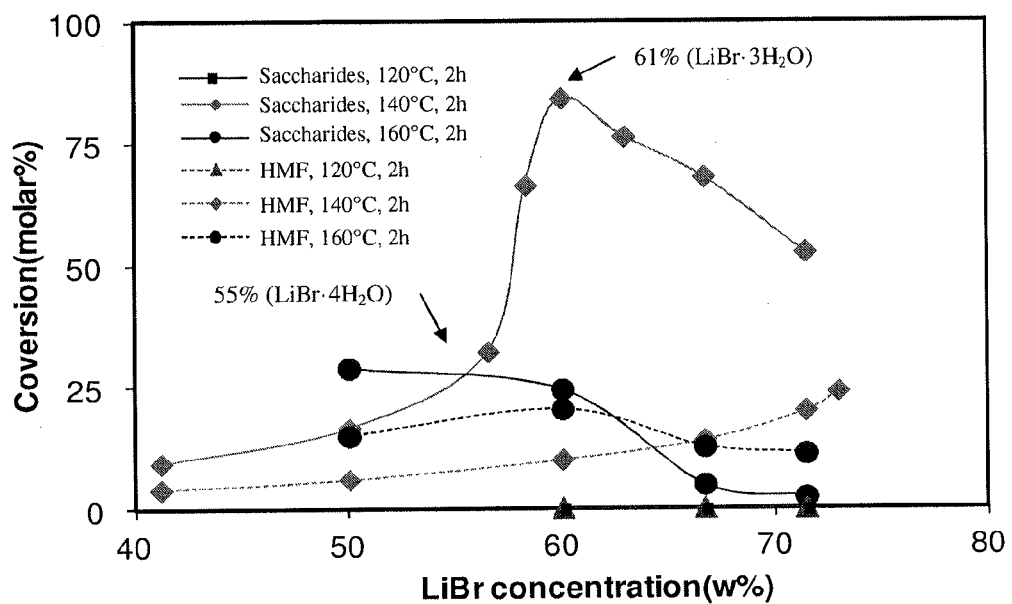
FIG. 3 is a graph illustrating hydrolysis of spruce powder in LiBr solution (no added acid) as a function of LiBr concentration at different conditions. In these hydrolysis assays, selected amounts of LiBr (700, 1000, 1300, 1400, 1500, 1700, 2000 or 2500 mg) were dissolved in 1 mL water in a 15-ml vial. Spruce powder (100 mg, 40 mesh) was added to the solutions and then vortexed to mix well. Samples were heated at 100~160° C. and stirred for 2 hours. After the completion of reaction, hydrolysate was filtered and the residue was washed with water. Filtrate and washings were collected for glucose, HMF or furfural analysis by HPLC.

Entries 1 to 5 of Table 7 indicate that concentration of LiBr is important to the extent of hydrolysis of cellulose, which is consistent with the results shown in FIG. 3. When the LiBr concentration is above 55% (for example, 60, 56, and 55% in entries 1, 2, and 3, respectively), the conversion/hydrolysis of polysaccharides was complete. Lower LiBr concentration (for example, 50 and 44% in entries 4 and 5, respectively) resulted in decreased conversion of polysaccharides. The results in Table 5 indicate that 55%, where the molar ratio of $H_2O$ to LiBr is 4 (e.g. $LiBr.4H_2O$) is the preferred minimum concentration of LiBr to dissolve and hydrolyze cellulose. Though acid addition and higher temperatures can further enhance the hydrolysis, LiBr concentration is an important parameter. When LiBr concentration is lower than 55%, increasing temperature or acid loading was unable to achieve desirable preferred high levels of hydrolysis in reasonable times, as shown by the results of entries 4, 5, 8 and 15.

Example 7

Effect of Acid and Temperature

Acid addition and higher temperature can enhance the hydrolysis of biomass in LiBr solution. For example, compared to the results in Example 4, entries 1 and 6 in Table 7 show that addition of 2% hydrochloric acid (w/w on spruce powder) can completely hydrolyze spruce in 60% LiBr solution in less than 10 min.

TABLE 7

Hydrolysis of spruce powder under varied conditions

| Entry | LiBr (g) | HCl* (mg) | Tem. (° C.) | Time (min) | Ara. (%) | Gal. (%) | Glu. (%) | Xyl. (%) | Man. (%) | HMF (%) | Fur. (%) | Res. (%) | Con. (%) | TSY (%) | TFY (%) |
|---|---|---|---|---|---|---|---|---|---|---|---|---|---|---|---|
| 0 | / | / | / | / | 0.98 | 2.34 | 42.03 | 5.18 | 10.18 | / | / | 26.88 | / | / | / |
| 1 | 7.50 | 10 | 140 | 10 | 0.80 | 1.79 | 30.51 | 2.55 | 6.29 | 5.29 | 2.45 | 24.85 | 100 | 67 | 12 |
| 2 | 6.25 | 10 | 140 | 10 | 0.80 | 1.81 | 30.22 | 2.44 | 6.01 | 6.00 | 3.25 | 25.65 | 100 | 66 | 15 |
| 3 | 6.00 | 10 | 140 | 10 | 0.83 | 1.84 | 30.96 | 2.84 | 6.39 | 4.50 | 2.53 | 26.12 | 100 | 69 | 11 |
| 4 | 5.00 | 10 | 140 | 10 | 1.05 | 2.17 | 13.01 | 3.81 | 7.49 | 1.86 | 2.27 | 42.31 | 76 | 44 | 7 |
| 5 | 4.00 | 50 | 140 | 20 | 0.18 | 0.90 | 13.98 | 0 | 1.95 | 1.62 | 1.99 | 49.63 | 64 | 27 | 6 |
| 6 | 7.50 | 10 | 140 | 5 | 0.89 | 1.95 | 34.43 | 3.73 | 7.05 | 3.2 | 2.02 | 24.78 | 100 | 77 | 8 |
| 7 | 6.00 | 50 | 120 | 10 | 0.66 | 1.72 | 27.61 | 1.64 | 4.79 | 4.05 | 2.78 | 32.31 | 91 | 58 | 11 |
| 8 | 5.00 | 50 | 120 | 10 | 0.96 | 2.30 | 18.26 | 2.95 | 7.39 | 1.69 | 3.04 | 36.54 | 85 | 51 | 8 |
| 9 | 7.50 | 10 | 120 | 25 | 0.81 | 1.82 | 31.69 | 3.00 | 6.32 | 3.28 | 2.24 | 30.12 | 95 | 70 | 9 |
| 10 | 6.25 | 5 | 160 | 5 | 1.01 | 2.08 | 36.68 | 4.41 | 8.05 | 2.98 | 1.58 | 22.65 | 100 | 84 | 7 |
| 11 | 6.25 | 5 | 150 | 5 | 1.03 | 2.05 | 35.20 | 4.68 | 8.21 | 1.65 | 0.88 | 23.21 | 100 | 82 | 4 |
| 12 | 6.25 | 5 | 140 | 5 | 1.10 | 1.99 | 27.76 | 4.94 | 7.72 | 0.66 | 0.57 | 23.82 | 100 | 70 | 2 |
| 13 | 7.50 | 10 | 100 | 60 | 0.98 | 2.02 | 36.59 | 4.17 | 8.48 | 1.31 | 1.01 | 26.32 | 100 | 84 | 4 |
| 14 | 7.50 | 50 | 100 | 10 | 0.90 | 1.96 | 34.23 | 3.69 | 7.71 | 1.68 | 1.46 | 25.65 | 100 | 78 | 5 |

TABLE 7-continued

Hydrolysis of spruce powder under varied conditions

| Entry | LiBr (g) | HCl* (mg) | Tem. (° C.) | Time (min) | Ara. (%) | Gal. (%) | Glu. (%) | Xyl. (%) | Man. (%) | HMF (%) | Fur. (%) | Res. (%) | Con. (%) | TSY (%) | TFY (%) |
|---|---|---|---|---|---|---|---|---|---|---|---|---|---|---|---|
| 15 | 5.00 | 25 | 140 | 15 | 0.32 | 1.17 | 17.52 | 0.06 | 2.41 | 2.68 | 3.06 | 41.01 | 78 | 34 | 9 |
| 16 | 7.50 | 50 | 110 | 5 | 1.16 | 2.36 | 43.38 | 5.06 | 9.97 | 1.41 | 1.15 | 27.12 | 100 | 99 | 4 |
| 17 | 7.50 | 25 | 110 | 5 | 1.16 | 2.38 | 42.46 | 5.18 | 9.71 | 0.98 | 0.86 | 26.93 | 100 | 98 | 3 |

Note:
"Tem." denotes temperature;
"Ara." denotes arabinose;
"Gal." denotes galactose;
"Glu." denotes glucose;
"Xyl." denotes xylose;
"Man." denotes mannose;
"HMF." denotes hydroxymethylfurfural;
"Fur." denotes furfural;
"Res" denote residues (lignin and unhydrolyzed polysaccharides) after reaction;
"Con." denotes conversion;
"TSY" denotes total monosaccharide yield;
"TFY" denotes total furan compounds (HMF and furfural) yield;
Reaction procedure: the chemical reagents list in each entry in Table 5 were added into 5 mL water and stirred to dissolve well. To this solution, 0.5 g spruce powder was added and stirred to react for certain time period list in each entry. "*" the amount of HCl is the absolute weight of hydrogen chloride.
"Ara.", "Gal.", "Glu.", "Xyl.", "Man.", "HMF." "Fur.", and "Res" (%) are weight percentage based on original feedstocks.
"con", "TSY", and "TFY"(%) are molar percentage based on total sugar content in feedstocks As shown in entries 10 to 12 of Table 7, satisfactory conversion could be achieved at higher temperature even with low acid loading (1% on biomass) in 56% LiBr solution. From entries 1 to 14, it can be seen that 100% conversion/dissolution of polysaccharides were achieved in some entries, but the yield of sugars was lower than theoretical, because either the polysaccharides were not completely hydrolyzed to monosaccharides (partially still in form of oligosaccharides) or part of the sugars were further degraded to furfural and HMF.

Extending reaction time or elevating temperature generally generated more HMF and furfural. It is thus not preferred to add more acid and increase temperature at the same time. At higher LiBr concentration, for example 60%, two options are available to achieve both high conversion yield and high sugar yield with a low yield of furan compounds in a relatively short time: (1) high temperature (150-160° C.) with low acid loading (1%), such as in entries 10 and 11; or (2) high acid loading (5-10% on biomass) at low temperature (110° C.), such as in entries 16 and 17. As shown in Table 5, up to 96% sugar yield was obtained at the conditions used in entries 16 and 17 with very limited degradation of sugars. Since the use of low temperature saves energy, the conditions of entries 16 and 17 are generally more preferred.

Example 8

Saccharification of Biomass in Concentrated LiBr Solution in Batch-Feed Mode to Increase Sugar Concentration In order to increase production efficiency and decrease LiBr/sugars separation cost in downstream processing, high feedstock loading (low ratio of LiBr solution to feedstock solid) is desirable, which will lead to a high concentration of end sugar solution. However, one-time addition of too much feedstock can cause mixing and mass transfer problems and therefore affect the hydrolysis efficiency and yield. In order to overcome such problems, feedstock was added in batch-feed mode to ensure that there is enough liquid available to wet added biomass and hydrolyze cellulose. The reactors employed for such processes can be any batch reactor, flow reactor, continuous stirred-tank reactor (CSTR), twin-screw extruder or any other reactors that can be operated in continuous or semi-continuous feeding mode. One or ordinary skill in the art understands and can employ all such reactors in application of the process of this invention.

In the present example, biomass feedstock was fed into a reactor as soon as the last batch was close to complete liquefaction/hydrolysis. From entries 1 to 5 in Table 8, 1, 2, 3, 4 and 5 g spruce powder, respectively, were added into 60% LiBr solution (7.5 g LiBr+5 mL water) (feeding procedure is described in the note under the Table 6, 0.5 g biomass per batch in an interval of 5 min). When total biomass feeding is below 4 g (entries 1 to 4), almost all spruce powder was hydrolyzed into monosaccharides with high selectivity. However, when 5 g spruce powder was fed, the conversion decreased likely because high solid loading and the accumulated lignin residue in hydrolysate made stirring difficult and decreased mass transport. If efficient mixing is provided, however, the upper limit of total biomass loading can increased, and the hydrolysis yield at high feedstock loading can be improved.

In entries 6 and 7 of Table 8, poplar and corn stover powder were also completely hydrolyzed into monosaccharides at the same conditions and procedure for entry 4. Because the hydrolysis was a heterogeneous reaction process, the size of biomass particles employed has a significant influence on the hydrolysis rate. When the particle size of poplar and corn stover chips was increased to 2-5 mm, they were still hydrolyzed, but hydrolysis yield decreased to around 90%, as shown in entries 8 and 9, respectively. This yield is lower than that in entries 6 and 7 where 40-mesh biomass powder was used. Extending reaction time or more efficient mixing can be employed to improve hydrolysis when larger particle sizes of biomass are used.

TABLE 8

Hydrolysis of spruce powder in batch-feed mode

| Entry | LiBr (g) | HCl* (mg) | Tem. (° C.) | Bio-mass (g) | Time (min) | Ara. (%) | Gal. (%) | Glu. (%) | Xyl. (%) | Man. (%) | HMF (%) | Fur. (%) | Res. (%) | Con. (%) | TSY (%) | TFY (%) |
|---|---|---|---|---|---|---|---|---|---|---|---|---|---|---|---|---|
| 0 | / | / | / | / | / | 0.98 | 2.34 | 42.03 | 5.18 | 10.18 | / | / | 26.88 | | | |
| 1 | 7.5 | 50 | 110 | 1 | 20 | 1.14 | 2.31 | 42.89 | 5.11 | 10.02 | 1.22 | 0.88 | 26.92 | 100 | 98 | 3 |
| 2 | 7.5 | 50 | 110 | 2 | 40 | 1.07 | 2.36 | 42.22 | 5.13 | 9.69 | 1.12 | 1.03 | 26.34 | 100 | 97 | 3 |
| 3 | 7.5 | 50 | 110 | 3 | 60 | 0.98 | 2.03 | 41.30 | 5.04 | 9.78 | 1.06 | 1.25 | 25.78 | 100 | 95 | 4 |
| 4 | 7.5 | 70 | 110 | 4 | 80 | 1.21 | 2.11 | 41.75 | 5.09 | 9.82 | 0.94 | 1.31 | 25.19 | 100 | 95 | 4 |
| 5 | 7.5 | 70 | 110 | 5 | 100 | 0.94 | 2.05 | 41.93 | 5.11 | 9.78 | 0.97 | 1.25 | 27.07 | 92 | 86 | 3 |
| 6 | 7.5 | 50 | 110 | 4 | 80 | 0.24 | 0.45 | 42.81 | 12.24 | 2.27 | 0.87 | 1.01 | 19.11 | 100 | 99 | 2 |
| 7 | 7.5 | 50 | 110 | 4 | 80 | 2.01 | 0.86 | 35.22 | 17.34 | 0 | 0.67 | 1.55 | 16.24 | 100 | 99 | 5 |
| 8 | 7.5 | 50 | 110 | 4 | 80 | 0.25 | 0.44 | 39.32 | 11.35 | 2.06 | 0.77 | 1.23 | 25.25 | 90 | 90 | 4 |
| 9 | 7.5 | 50 | 110 | 4 | 80 | 2.12 | 0.99 | 32.21 | 16.12 | 0 | 0.69 | 1.61 | 23.27 | 91 | 89 | 4 |

Note:
Entries 1 to 5: spruce powder; entry 6: poplar powder; entry 7: corn stover powder; entry 8: poplar chips (0.2~0.5 cm); entry 9: corn stover chips (0.2~0.5 cm).
"Tem." denotes temperature;
"Ara." denotes arabinose;
"Gal." denotes galactose;
"Glu." denotes glucose;
"Xyl." denotes xylose;
"Man." denotes mannose;
"HMF." denotes hydroxymethylfurfural;
"Fur." denotes furfural;
"Res" denote residues (lignin and unhydrolyzed polysaccharide) after reaction;
"Con." denotes conversion;
"TSY." denotes total monosaccharides yield;
"TFY." denotes total furan compounds (HMF and furfural) yield.
*the amount of HCl is the absolute weight of Hydrogen chloride.
Reaction procedure: 7.5 g LiBr and 50 mg concentrated HCl were dissolved into 5 mL water and stirred until clear solution was obtained. To this solution, 0.5 g biomass was added each batch at an interval of 5 min with stirring. After the addition of feedstock, hydrolysis was allowed to proceed at a total time (from the first feedstock addition to the end of reaction) listed in the Table. For entries 4 to 8, after the sixth feeding, additional 20 mg HCl were added and reactions were allowed to proceed for 10-30 min before next addition. The composition of original poplar and corn stover is shown in Table 1.
"Ara.", "Gal.", "Glu.", "Xyl.", "Man.", "HMF." "Fur.", and "Res" (%) are weight percentage based on original feedstocks.
"con", "TSY", and "TFY"(%) are molar percentage based on total sugar content in feedstocks.

Example 9

Saccharification of Biomass in Concentrated Solution of Different Salts

Hydrolysis of biomass in different metal halide solutions was investigated. Results in Table 9 show that when the concentration of salt was 60%, LiCl, LiBr and $CaBr_2$ could give complete conversion/hydrolysis of polysaccharides. $CaBr_2$ is as effective as LiBr in this experiment. In addition, experiments with separation methods discussed below indicate that exemplary methods for separating LiBr from sugars, also work with $CaBr_2$ 1. Furthermore, $CaBr_2$ is currently much cheaper than LiBr and as such is currently preferred.

Although LiCl also gave a complete conversion, the solubility of LiCl in water is significantly lower than that of LiBr. For example, the solubility of LiBr in water at 90° C. is about 254 g/100 mL, while that of LiCl at 100° C. is about 128 g/100 mL. As a consequence, 60% LiCl starts crystallizing at 120° C., which makes downstream separation operations difficult. $ZnCl_2$ and $CaCl_2$ only gave a conversion of 50~70%, which is consistant with the reports by Penque and Chen[10c, 10d].

TABLE 9

Effect of different salts on hydrlysis of biomass

| Salt | Conversion, % |
|---|---|
| LiBr | 100 |
| LiCl | 100 |
| $CaBr_2$ | 100 |
| $ZnBr_2$ | 66 |
| $ZnCl_2$ | 60 |
| $MgBr_2$ | 75 |
| $CaCl_2$ | 70 |
| NaBr | 68 |

Note:
reaction condition: 1 ml $H_2O$, 1500 mg salt, 100 mg spruce powder, 2 mg HCl, 140° C., and 30 min.

Example 10

Saccharification of Biomass in Concentrated LiBr Solution with Different Acids Addition of acid could significantly enhance the hydrolysis of lignocellulose material in concentrated LiBr solution, as discussed above. Here different acids were tested for their efficiency in hydrolysis of spruce powder in 60% LiBr solution. It can be seen from Table 10 that strong acids such as sulfuric acid and nitric acid are as effective as hydrochloric acid in catalyzing the hydrolysis of spruce, while weak acids gave a decreased hydrolysis yield. For example, acetic acid had a yield of 90% at the same conditions.

TABLE 10

Effect of different acids on hydrlysis of biomass

| Acid | Conversion, % |
|---|---|
| HCl | 100 |
| $H_2SO_4$ | 100 |

TABLE 10-continued

Effect of different acids on hydrlysis of biomass

| Acid | Conversion, % |
|---|---|
| $HNO_3$ | 100 |
| $H_3PO_4$ | 95 |
| HCOOH | 96 |
| $CH_3COOH$ | 90 |

Note:
reaction condition: 1 ml $H_2O$, 1500 mg LiBr, 100 mg spruce powder, 2 mg acid, 140° C., 30 min.

Example 11

Optimization of Spruce Saccharification in LiBr Solution

Saccharification of spruce in LiBr solution was optimized for biomass conversion using response surface methodology (RSM) experimental design[19] within the range of LiBr concentration 52.5-67.5%, HCl loading 1.5-4.5% (on biomass), temperature 105-130° C., and time 15-45 min. Conditions and results are summarized in Table 11. The optimal results for spruce saccharification within the ranges in this experiment were 60% LiBr, 3% HCl loading, 120° C. and 30 min.

Example 12

Optimization of Spruce Saccharification in $CaBr_2$

It has been found that $CaBr_2$ can be as effective as LiBr in saccharification of lignocellulosic biomass. To optimize the process conditions for biomass conversion, experimental matrixes were designed using RSM to determine optimal conditions for saccharification in $CaBr_2$ solution. The experimental matrix shown in Table 12 includes 21 experiments, designed within a wide range of process conditions: $CaBr_2$ concentration 46-74%, HCl loading 1.2-6.8% (on biomass), temperature 102-158° C., and time 12-68 min. These results indicated that the conditions: 60% $CaBr_2$, 4% HCl loading, 130° C. and 40 min was optimal for spruce saccharification in terms of biomass conversion. However, the yields of furfural and HMF were higher than desired compared to saccharides. The conditions optimized for biomass conversion are believed to be overly severe, resulting in significant sugar degradation.

To fine-tune the conditions to optimize for minimized furfural and HMF production, a second matrix was designed, as shown in Table 13. In this design, reaction time was fixed at 40 min, and condition severity was reduced slightly. Other conditions were then optimized within the range of $CaBr_2$ concentration 53-68%, HCl loading 1-4% (on biomass), and temperature 110-140° C. The results in Tables 12 and 13 indicate that the condition of 60% $CaBr_2$, 2.5% HCl loading, 125° C. and 40 min is optimal for spruce saccharification in $CaBr_2$ solution with minimization of the yield of furfural and HMF.

Example 13

Extraction of Sugar from LiBr-Sugar Solution with Boronic Acid

The chemical saccharification process presented herein uses concentrated aqueous LiBr solution, or concentrated aqueous solutions of other bromine salts, s as a medium. Effective separation of sugars and salt after saccharification is an important aspect of industrial application of the process. LiBr is quite different from sugars in physical and chemical properties, which can be used to separate LiBr from sugars.

Boronic acid can react with the cis-diol structure of sugars in the presence of lipophilic quaternary alkyl amine to form a stable boronic acid-sugar complex under alkali condition. The complex is soluble in organic solvent and can be extracted with hexane. The salt remains in the aqueous phase. The mechanism of this method is shown in Scheme 2. The boronic acid-sugar complex is stable under alkaline condition, but unstable under acidic condition. Therefore, the sugar extracted into the organic phase can be recovered by stripping the organic phase with acidic water. The boronic acid remaining in the organic phase can then be used in the next batch extraction.

Scheme 2: Mechanism of extraction of glucose with boronic acid

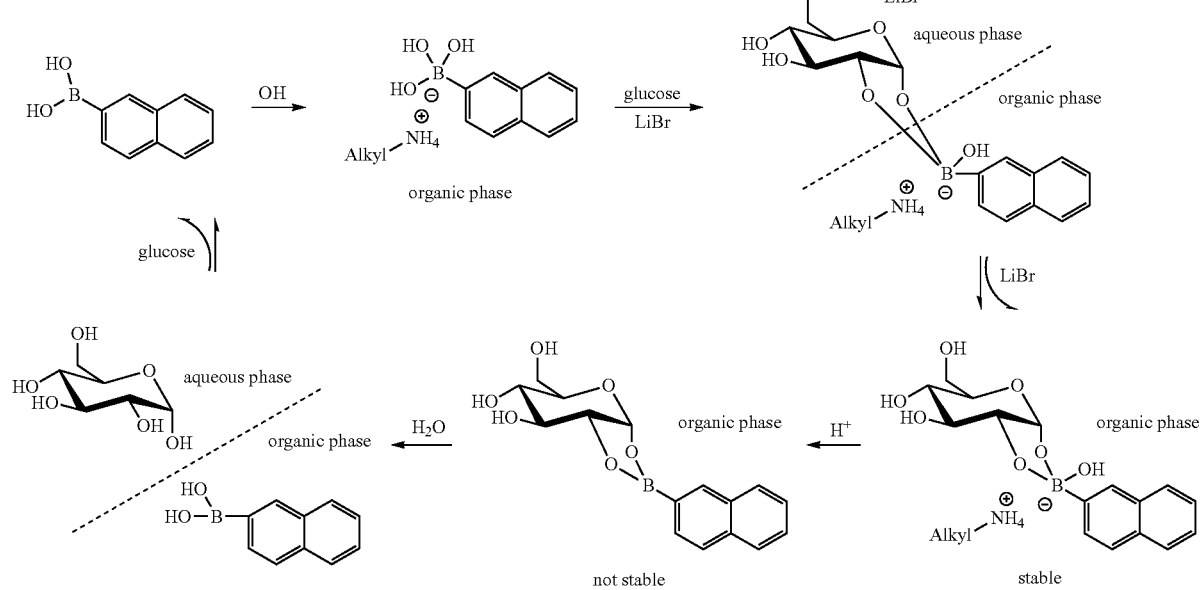

TABLE 11

Experimental matrix for optimizing saccharification of spruce in LiBr solution

| Run | LiBr % | HCl % | Tem °C. | Time min | Gal. % | Ara. % | Glu. % | Xyl. % | Man. % | HMF % | Fur. % | Res. % | Con. % |
|---|---|---|---|---|---|---|---|---|---|---|---|---|---|
| 1 | 60 | 3 | 120 | 30 | 1.92 | 0.98 | 41.75 | 5.33 | 10.34 | 1.37 | 0.58 | 26.17 | 100.00 |
| 2 | 60 | 3 | 120 | 30 | 1.97 | 1.03 | 41.46 | 5.31 | 10.31 | 1.41 | 0.54 | 26.12 | 100.00 |
| 3 | 55 | 4 | 130 | 40 | 1.54 | 0.9 | 35.62 | 4.95 | 9.19 | 2.3 | 0 | 32.8 | 91.80 |
| 4 | 60 | 3 | 120 | 30 | 1.93 | 1.03 | 41.68 | 5.29 | 10.31 | 1.33 | 0.51 | 26.85 | 100.00 |
| 5 | 60 | 3 | 120 | 30 | 1.93 | 1.05 | 41.78 | 5.27 | 10.28 | 1.34 | 0.55 | 26.98 | 100.00 |
| 6 | 60 | 4.5 | 120 | 30 | 1.66 | 1 | 35.08 | 3.98 | 8.81 | 1.84 | 1.19 | 34.28 | 89.57 |
| 7 | 60 | 3 | 120 | 45 | 1.91 | 0.96 | 40.49 | 4.03 | 10.11 | 2.14 | 1.2 | 26.83 | 100.00 |
| 8 | 60 | 3 | 105 | 30 | 1.83 | 0.85 | 40.23 | 5.05 | 9.62 | 0.68 | 0.12 | 29.78 | 96.36 |
| 9 | 55 | 2 | 130 | 20 | 1.86 | 0.91 | 40.74 | 4.36 | 9.7 | 1.75 | 1 | 28.43 | 98.40 |
| 10 | 65 | 2 | 130 | 40 | 2.29 | 0.95 | 37.81 | 4.15 | 9.39 | 1.9 | 1.06 | 30.15 | 95.80 |
| 11 | 65 | 4 | 110 | 20 | 2.26 | 0.87 | 38.06 | 4.12 | 9.34 | 1.66 | 0.89 | 31.12 | 94.34 |
| 12 | 60 | 3 | 120 | 30 | 1.98 | 1.06 | 40.95 | 5.29 | 10.35 | 1.3 | 0.55 | 26.8 | 100.00 |
| 13 | 60 | 3 | 120 | 15 | 1.87 | 0.91 | 35.96 | 4.32 | 8.78 | 0.95 | 0.43 | 35.07 | 88.37 |
| 14 | 55 | 4 | 110 | 40 | 1.64 | 0.93 | 36.26 | 4.81 | 8.98 | 0.61 | 0 | 33.85 | 90.22 |
| 15 | 55 | 2 | 110 | 20 | 1.24 | 0.84 | 36.11 | 4.73 | 8.79 | 0 | 0 | 35.13 | 88.28 |
| 16 | 60 | 1.5 | 120 | 30 | 1.61 | 0.93 | 38.61 | 5.08 | 9.52 | 0.09 | 0 | 30.6 | 95.12 |
| 17 | 67.5 | 3 | 120 | 30 | 2.18 | 0.81 | 31.35 | 4.11 | 8.23 | 2.14 | 0.33 | 38.68 | 82.92 |
| 18 | 65 | 2 | 110 | 40 | 2.13 | 0.91 | 37.95 | 4.98 | 9.48 | 0.85 | 0.14 | 30.23 | 95.68 |
| 19 | 60 | 3 | 135 | 30 | 1.93 | 0.81 | 32.65 | 3.22 | 8.17 | 3.64 | 1.85 | 36.17 | 86.71 |
| 20 | 52.5 | 3 | 120 | 30 | 1.5 | 0.82 | 32.4 | 4.32 | 8.45 | 0.45 | 0 | 38.62 | 83.01 |
| 21 | 65 | 4 | 130 | 20 | 2.38 | 0.84 | 33.38 | 3.62 | 8.46 | 2.46 | 1.22 | 36.22 | 86.64 |

Note:
(1) HCl is the loading of hydrochloric acid (pure) on dry matter of biomass.
(2) "Tem." denotes temperature; "Ara." denotes arabinose; "Gal." denotes galactose; "Glu." denotes glucose; "Xyl." denotes xylose; "Man." denotes mannose; "HMF." denotes hydroxymethylfurfural; "Fur." denotes furfural; "Res" denote residues (lignin and unhydrolyzed polysaccharides) after reaction; "Con." denotes conversion.
(3) In these experiments, a certain amount of LiBr was added to 4 mL $H_2O$, and 600 mg spruce powder was added to the solution.
(4) "Gal.", "Ara.", "Glu.", "Xyl.", "Man.", "HMF", "Furfural" and "Res." are weight percentage based on original feedstock.
(5) conversion = (1-moisture %-residue %)/(1-moisture %-lignin %).

TABLE 12

Experimental matrix for optimizing saccharification of spruce in $CaBr_2$ solution

| Run | $CaBr_2$ % | HCl % | Temp. °C. | Time min | Ara. % | Gal. % | Glu. % | Xyl. % | Man % | HMF % | Fur. % | Res. % | Con. % |
|---|---|---|---|---|---|---|---|---|---|---|---|---|---|
| 1 | 46 | 4 | 130 | 40 | 0.35 | 0.83 | 13.76 | 1.90 | 3.23 | 0.95 | 1.17 | 64.00 | 44.69 |
| 2 | 50 | 6 | 110 | 60 | 0.47 | 1.06 | 20.37 | 2.58 | 4.19 | 0.89 | 1.02 | 54.42 | 59.16 |
| 3 | 70 | 2 | 150 | 60 | 0.89 | 1.90 | 29.85 | 3.43 | 8.02 | 3.92 | 1.23 | 34.57 | 89.13 |
| 4 | 60 | 1.2 | 130 | 40 | 0.55 | 1.29 | 25.43 | 2.91 | 5.75 | 3.87 | 1.73 | 41.42 | 78.79 |
| 5 | 60 | 4 | 130 | 40 | 0.98 | 2.19 | 34.31 | 3.93 | 8.43 | 4.36 | 2.33 | 28.25 | 98.67 |
| 6 | 60 | 4 | 130 | 68 | 0.67 | 1.41 | 25.73 | 2.75 | 5.63 | 5.15 | 3.03 | 40.02 | 80.90 |
| 7 | 60 | 4 | 102 | 40 | 0.33 | 0.78 | 13.69 | 2.88 | 3.17 | 0 | 0 | 65.32 | 42.70 |
| 8 | 60 | 4 | 130 | 40 | 0.95 | 2.28 | 34.36 | 3.85 | 8.28 | 4.27 | 2.40 | 28.03 | 99.00 |
| 9 | 50 | 6 | 150 | 60 | 0.65 | 1.34 | 26.17 | 3.91 | 5.92 | 1.17 | 0.89 | 44.70 | 73.83 |
| 10 | 50 | 2 | 150 | 20 | 0.43 | 0.99 | 19.50 | 2.35 | 3.95 | 0.86 | 1.05 | 55.23 | 57.93 |
| 11 | 50 | 2 | 110 | 20 | 0.32 | 0.79 | 12.65 | 2.07 | 3.17 | 0 | 0 | 68.38 | 38.08 |
| 12 | 60 | 4 | 130 | 40 | 0.94 | 2.15 | 34.17 | 4.03 | 8.51 | 4.32 | 2.27 | 28.88 | 97.72 |
| 13 | 70 | 2 | 110 | 60 | 0.91 | 2.03 | 33.59 | 4.25 | 8.47 | 1.39 | 0.92 | 32.30 | 92.56 |
| 14 | 60 | 4 | 130 | 40 | 1.01 | 2.07 | 34.42 | 4.08 | 8.38 | 4.14 | 2.34 | 28.72 | 97.96 |
| 15 | 70 | 6 | 110 | 20 | 0.91 | 1.95 | 32.83 | 3.98 | 8.39 | 1.33 | 0.95 | 33.37 | 90.94 |
| 16 | 60 | 4 | 158 | 40 | 0.87 | 1.92 | 27.41 | 1.62 | 7.17 | 6.32 | 3.75 | 35.56 | 87.63 |
| 17 | 60 | 4 | 130 | 40 | 0.95 | 2.17 | 33.87 | 3.91 | 8.35 | 4.27 | 2.43 | 29.3 | 97.09 |
| 18 | 60 | 6.8 | 130 | 40 | 0.57 | 1.17 | 22.49 | 2.27 | 5.32 | 4.14 | 2.25 | 46.72 | 70.78 |
| 19 | 60 | 4 | 130 | 12 | 0.87 | 1.98 | 32.95 | 4.77 | 8.71 | 2.85 | 2.32 | 30.53 | 95.23 |
| 20 | 70 | 6 | 150 | 20 | 0.49 | 1.02 | 24.43 | 3.13 | 4.92 | 2.94 | 1.23 | 48.28 | 68.43 |
| 21 | 74 | 4 | 130 | 40 | 0.68 | 1.51 | 27.79 | 3.34 | 6.54 | 5.95 | 2.54 | 36.23 | 86.62 |

Note:
(1) HCl is the loading of hydrochloric acid (pure) on dry matter of biomass.
(2) "Tem." denotes temperature; "Ara." denotes arabinose; "Gal." denotes galactose; "Glu." denotes glucose; "Xyl." denotes xylose; "Man." denotes mannose; "HMF." denotes hydroxymethylfurfural; "Fur." denotes furfural; "Res" denote residues (lignin and unhydrolyzed polysaccharides) after reaction; "Con." denotes conversion.
(3) In these experiments, a certain amount of LiBr was added to 4 mL $H_2O$, and 600 mg spruce powder was added to the solution.
(4) "Gal.", "Ara.", "Glu.", "Xyl.", "Man.", "HMF", "Furfural" and "Res." are weight percentage based on original feedstock.
(5) conversion = (1-moisture %-residue %)/(1-moisture %-lignin %).

TABLE 13

Experimental matrix for optimizing saccharification of spruce in CaBr$_2$ solution to minimize furfural and HMF

| Run | CaBr$_2$ % | HCl % | Temp. °C. | Ara. % | Gal. % | Glu. % | Xyl. % | Man. % | HMF % | Fur. % | Res. % | Con. % |
|---|---|---|---|---|---|---|---|---|---|---|---|---|
| 1  | 60 | 2.5 | 125 | 1.01 | 2.01 | 37.03 | 5.30 | 9.08 | 0.52 | 0.59 | 30.42 | 95.39 |
| 2  | 60 | 1   | 125 | 0.92 | 1.40 | 28.87 | 4.62 | 8.15 | 0.00 | 0.12 | 35.72 | 87.39 |
| 3  | 60 | 2.5 | 140 | 0.95 | 1.67 | 33.47 | 4.34 | 8.47 | 2.76 | 1.73 | 33.70 | 90.44 |
| 4  | 60 | 2.5 | 125 | 0.99 | 1.95 | 37.12 | 5.28 | 9.11 | 0.53 | 0.55 | 31.03 | 94.47 |
| 5  | 60 | 4   | 125 | 1.00 | 1.99 | 33.48 | 4.97 | 8.43 | 1.61 | 1.23 | 31.95 | 93.08 |
| 6  | 65 | 1.5 | 135 | 1.02 | 2.08 | 36.43 | 5.10 | 9.21 | 1.21 | 0.88 | 30.20 | 95.73 |
| 7  | 55 | 1.5 | 115 | 0.76 | 1.87 | 24.08 | 4.05 | 7.54 | 0.00 | 0.00 | 43.47 | 75.69 |
| 8  | 60 | 2.5 | 125 | 0.97 | 1.95 | 37.07 | 5.23 | 9.14 | 0.54 | 0.49 | 30.95 | 94.59 |
| 9  | 65 | 3.5 | 115 | 0.88 | 1.85 | 26.83 | 4.11 | 8.85 | 0.89 | 0.88 | 35.20 | 88.18 |
| 10 | 60 | 2.5 | 125 | 0.99 | 2.00 | 36.98 | 5.31 | 9.08 | 0.54 | 0.65 | 29.58 | 96.66 |
| 11 | 68 | 2.5 | 125 | 0.85 | 1.48 | 26.76 | 4.50 | 7.67 | 0.71 | 0.73 | 36.63 | 86.02 |
| 12 | 55 | 3.5 | 135 | 0.75 | 1.72 | 23.02 | 3.37 | 7.11 | 1.87 | 1.79 | 40.15 | 80.70 |
| 13 | 60 | 2.5 | 125 | 0.98 | 2.03 | 37.17 | 5.27 | 9.05 | 0.55 | 0.66 | 29.78 | 96.36 |
| 14 | 60 | 2.5 | 110 | 0.81 | 1.62 | 25.75 | 4.07 | 7.43 | 0.39 | 0.43 | 38.08 | 83.83 |
| 15 | 53 | 2.5 | 125 | 0.65 | 1.22 | 14.97 | 2.80 | 4.22 | 0.17 | 0.41 | 56.90 | 55.41 |

Note:
(1) HCl is the loading of hydrochloric acid (pure) on dry matter of biomass.
(2) "Tem." denotes temperature; "Ara." denotes arabinose; "Gal." denotes galactose; "Glu." denotes glucose; "Xyl." denotes xylose; "Man." denotes mannose; "HMF." denotes hydroxymethylfurfural; "Fur." denotes furfural; "Res" denote residues (lignin and unhydrolyzed polysaccharides) after reaction; "Con." denotes conversion.
(3) In these experiments, a certain amount of LiBr was added to 4 mL H$_2$O, and 600 mg spruce powder was added to the solution.
(4) "Gal.", "Ara.", "Glu.", "Xyl.", "Man.", "HMF", "Furfural" and "Res." are weight percentage based on original feedstock.
(5) conversion = (1-moisture %-residue %)/(1-moisture %-lignin %).
(6) Reaction time was fixed at 40 min.

Naphthalene-2-boronic acid (N$_2$B) was used in this study. A glucose-LiBr solution (100 mg glucose and 500 mg LiBr in 1 mL buffer solution at pH=11) was tested. The organic phase was prepared by dissolving 100 mg N$_2$B and 200 mg Aliquat® 336 (a quaternary ammonium salt which has a mixture of C8 and C10 alkane chains) into 5 mL hexane/octanol (85/15, v/v). The sugar-LiBr solution (1 mL) was mixed with the organic solution (5 mL) and vortexed for 30 min to reach equilibrium. Then the mixture was centrifuged to separate the aqueous and organic phases. The organic phase was then stripped with 5 mL 1% HCl solution. Analysis of the stripping solution indicated that approximately 10 mg sugar was recovered through a single pass of extraction.

Example 14

Separation of LiBr and Sugars with Ion Exclusion Chromatography

Ion exclusion chromatography has been used to separate salt and sugars in industry. The process does not consume acid and alkali for resin regeneration as ion exchange chromatography does. Ion exclusion chromatography uses a resin that has the same anion or cation as the salt does. When a mixture of sugars and the salt is loaded on the ion exclusion column, because of the exclusion force between resin and the salt, the salt will elute out faster than sugars that do not have strong interaction with the resin, thus resulting in the separation of the salt and sugars.

Figure 4:
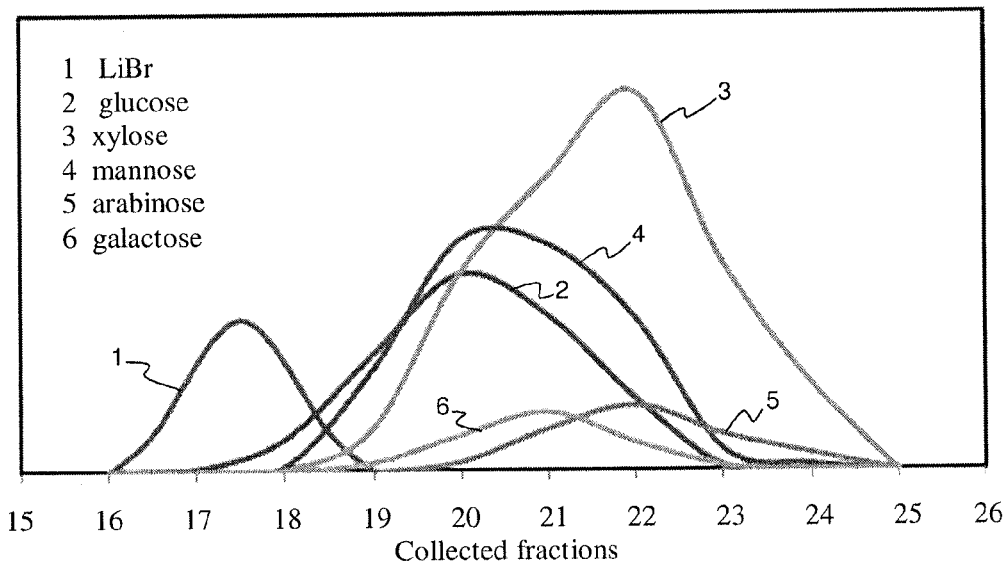
FIG. 4 is a graph illustrating separation of LiBr and sugar solution using ion-exclusion chromatography (arabinose: 10 mg; galactose: 10 mg; glucose: 80 mg; xylose: 20 mg; mannose: 20 mg, LiBr: 50 mg, water: 0.5 mL).

The experimental separation was performed on a glass column (diameter 2 cm; length 50 cm), packed with anion exchange resin (DOWEX 1×8-400, Cl$^-$ form) at room temperature. Prior to the test, the column was fully converted into Br$^-$ form by eluting with 400 ml of 0.2 N NaBr at a flow rate of 1.5 ml/min, followed by a thorough rinse with 2000 ml of deionized water. A LiBr-sugar solution (arabinose: 10 mg; galactose: 10 mg; glucose: 80 mg; xylose: 20 mg; mannose: 20 mg, LiBr: 50 mg, water: 0.5 mL) was loaded to the column and eluted with deionized water at a rate of 1.5 mL/min. AgNO$_3$ solution was used to monitor the elution of LiBr. Fractions of 2.5 mL were collected from the exit of the column, and their sugar profiles were determined off-line by HPLC. LiBr in each fraction was determined through titration. The profile in FIG. 4 shows that LiBr and sugars were separated very well, indicating that this method is an efficient way for separating sugars and LiBr.

Figure 5:
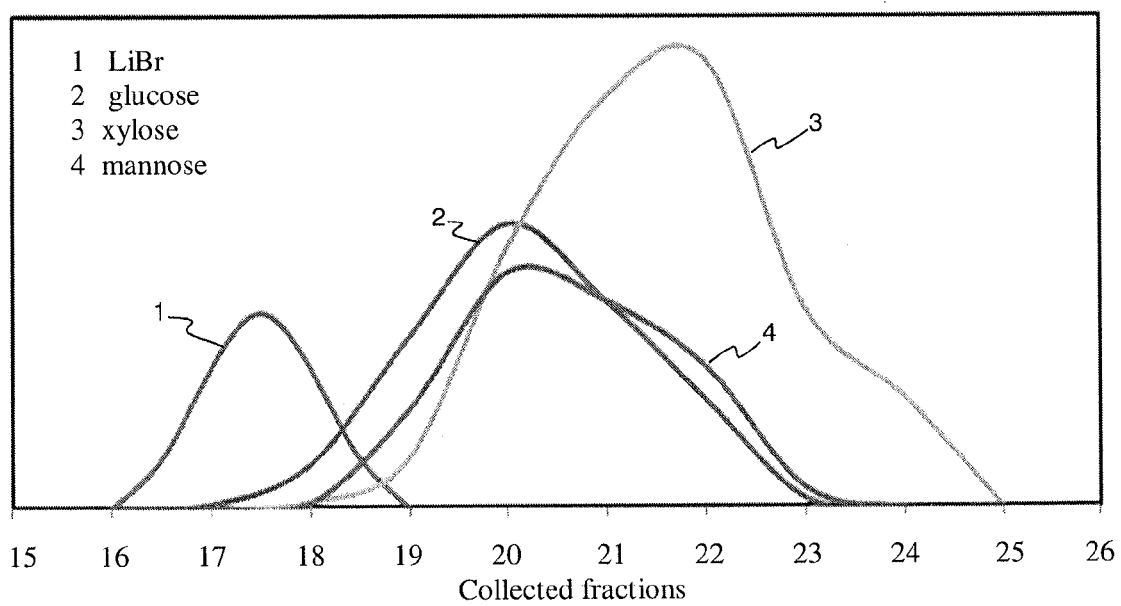
FIG. 5 is a graph illustrating separation of residual LiBr/sugar solution by Ion-exclusion chromatography (glucose: ~80 mg; xylose: ~15 mg; mannose: ~60 mg; LiBr: ~50 mg).
Figure 6:
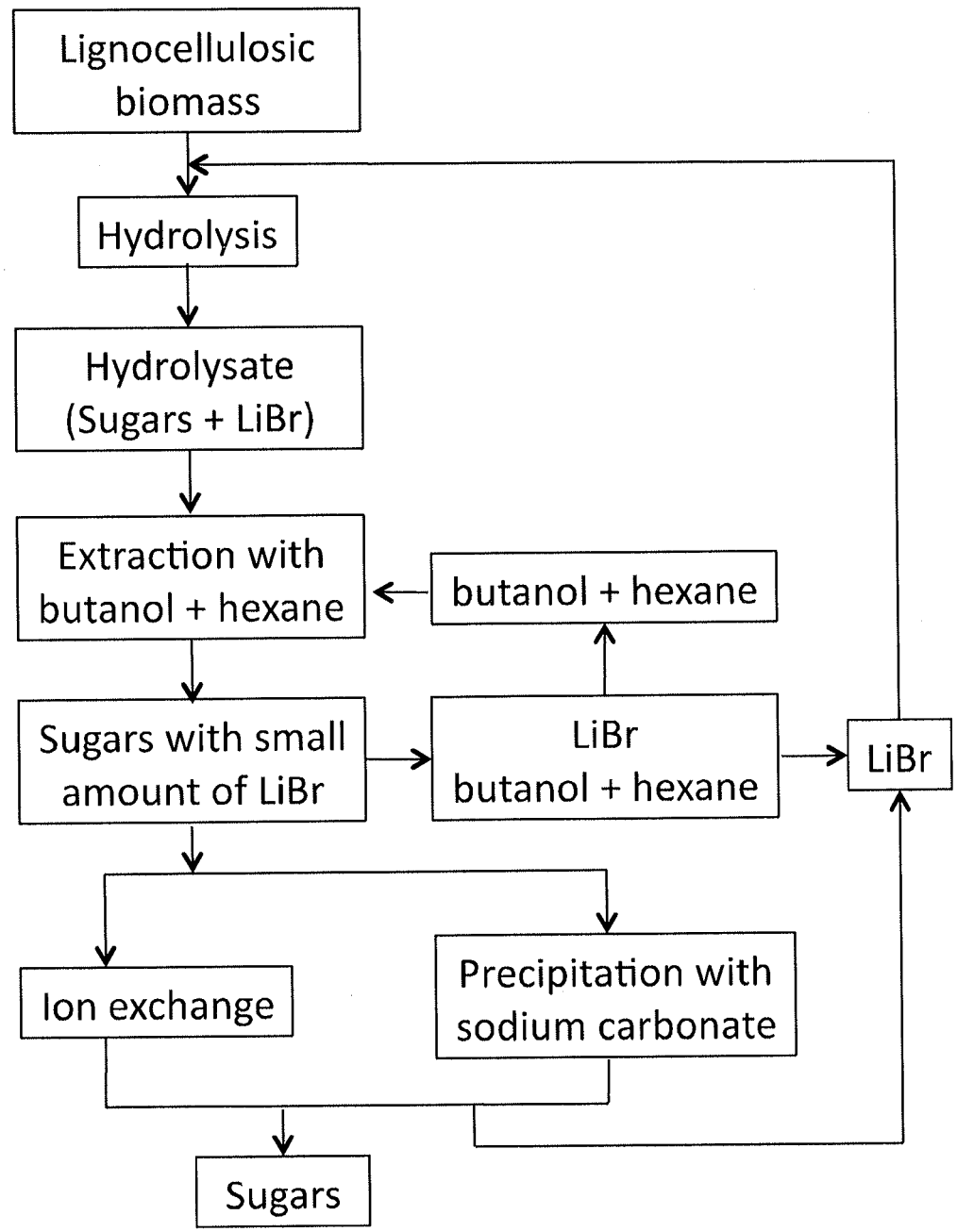
FIG. 6 is a flowchart for integrated methods to separate LiBr and sugars.

The ion exclusion method was also applied to a hydrolysate of spruce to separate LiBr from sugar products. After spruce was hydrolyzed in concentrated LiBr solution, most LiBr was removed from the hydrolysate by solvent extraction with butanol, as described below. The resulting solution of sugars still contained a small amount of LiBr. The residual LiBr can be removed from the sugars by the ion exclusion method. For example, an sample of the spruce hydrolysate containing ~80 mg glucose, ~15 mg xylose, ~60 mg mannose, and ~50 mg LiBr was diluted with water to a solution of 0.5 mL, and then was loaded on the column and eluted with deionized water at a rate of 1.5 mL/min. As shown in FIG. 5, LiBr and sugars could be separated cleanly. However, both sugars and LiBr were diluted during the elution, and their concentration after elution was only about 1%.

It is possible to separate concentrated LiBr and sugars directly using ion exclusion chromatography without pre-extraction of LiBr with butanol. However, because of the high concentration of LiBr used, a long ion exclusion column and a large amount of eluent (water) are needed to get a good separation. As the requirement for use of large amounts of eluent results in significantly diluted LiBr and sugar streams, the method is not currently preferred.

Example 15

Extraction of LiBr with Organic Solvents from LiBr-Sugar Solution

Direct separation of LiBr and sugars in a concentrated solution is very difficult because both components are highly soluble in water. However, LiBr and sugars have very different solubility in organic solvents (such as alcohol, ketone, and ether), in which LiBr is still highly soluble, but sugars are insoluble. It is thus possible to separate LiBr and sugars by extraction with water-immiscible organic solvent. Extraction of LiBr from brines by organic solvents, such as TBP (tributylphosphate)[15] and butanol[16] and $CaBr_2$ from brines by amine[17], has been reported.

In the present study, n-butanol was chosen as the extraction solvent for LiBr because of its relatively low price. LiBr is soluble, but sugars are insoluble in n-butanol. Since n-butanol is slightly soluble in water (63.2 g/L), when n-butanol is used to extract LiBr from an aqueous solution of LiBr and sugars, a small amount of water will be picked up into n-butanol layer. As a result, a small amount of sugars will be extracted into the n-butanol layer because of the presence of the water. To reduce the amount of sugars extracted by n-butanol, hexane can be used as a phase modifier. However, the inclusion of hexane inevitably decreases the solubility of LiBr in n-butanol because of decreased polarity of the organic phase. In addition, because of the strong interaction between LiBr and sugars in thick sugar syrup, it is almost impossible to completely remove LiBr by extraction alone. After the extraction, any small amount of LiBr in the sugar stream can be removed by means of ion exchange resin, crystallization, precipitation with anti-solvent, and precipitation with sodium carbonate, as described in Examples herein.

A: Extraction of LiBr from LiBr-Glucose Solution with n-Butanol

A LiBr-glucose solution was first used to test the butanol extraction. The results in Tables 14 and 15 indicate that not only LiBr, but also a small amount of glucose, was extracted into butanol. In addition, it was also observed that a small amount of water was picked up into the butanol phase. Since glucose is insoluble in pure butanol, extraction of glucose into butanol should be attributed to the presence of water in butanol. In order to reduce the extraction of glucose into the butanol phase, hexane was added to the butanol as a phase modifier to reduce the polarity of the solvent.

As shown in Table 14, as the ratio of hexane in butanol was increased, less glucose was extracted, but the extraction steps needed to achieve satisfactory extraction of LiBr increased. This is because the solubility of LiBr in n-butanol decreased when hexane was added due to the decreased polarity of the solvent. When the butanol to hexane ratio was increased to 7/3, about 10% glucose (~30 mg out of 320 mg glucose) was extracted into the butanol phase. Further increasing hexane did not significantly reduce the extraction of glucose, but substantially increased the extraction steps needed for removing LiBr, as shown in Table 15. Meanwhile, with the extraction of both LiBr and water into the organic phase, the volume of the hydrolysate decreased gradually, resulting in a thick sugar syrup. For example, at a butanol to hexane ratio of 7:3, LiBr content in the LiBr-glucose solution was reduced from 1500 mg to 250 mg after 10 extractions (see note under Table 14). Repeating the extraction procedure two more times (20 more extractions in total) could further decrease LiBr from 250 mg to 50 mg and from 50 mg to 30 mg, respectively. Further extraction could remove more LiBr, but it was very difficult to completely remove LiBr from glucose. This might be caused by a strong interaction between glucose and LiBr. With the removal of LiBr and water by the extraction, the glucose solution became a thick sugar syrup, and therefore extraction efficiency was decreased.

In summary, butanol-hexane extraction can effectively separate LiBr from glucose, but it is very difficult to remove LiBr completely by the extraction alone. It is more effective and economic to remove the residual LiBr in other ways, such as ion exchange, crystallization, and precipitation with anti-solvent or sodium carbonate, as described in Examples herein.

TABLE 14

Separation of glucose and LiBr by extraction with a mixture of butane and hexane

| Butanol:hexane (v/v) | Number of extraction step | Glucose retained after extraction, mg | Glucose retained/ extraction steps |
| --- | --- | --- | --- |
| 10:0 | 6 | 95 | 16 |
| 9:1 | 7 | 115 | 16.5 |
| 8.5:1.5 | 8 | 140 | 17.5 |
| 8:2 | 9 | 160 | 17.8 |
| 7.5:2.5 | 9 | 175 | 19.4 |
| 7:3 | 10 | 185 | 18.5 |
| 6.5:3.5 | 12 | 187 | 16 |
| 6:4 | 13 | 189 | 14.5 |
| 5:5 | 15 | 190 | 12.6 |

Note:
Glucose and LiBr solution (200 mg glucose and 1500 mg LiBr in 1 mL water) was extracted with butanol-hexane in a 10-mL screw capped vial. In each extraction, 1 mL organic solvent was added, and the vial was vortex for 1 min for extraction. Organic phase was separated from aqueous phase by centrifugation. When organic phase was removed, 1 mL fresh organic solvent was added for next extraction.

TABLE 15

Separation efficiency of LiBr and glucose by solvent extraction

| Butanol:hexane | Glucose extracted, mg | LiBr extracted, mg | LiBr/sugar |
| --- | --- | --- | --- |
| 10:0 | 20 | 383 | 19 |
| 9:1 | 12 | 310 | 26 |
| 8.5:1.5 | 7 | 277 | 40 |
| 8:2 | 5.5 | 252 | 46 |
| 7.5:2.5 | 5 | 231 | 46 |
| 7:3 | 4.5 | 216 | 48 |
| 6.5:3.5 | 4 | 195 | 49 |
| 6:4 | 3 | 152 | 51 |
| 5:5 | 2 | 141 | 71 |

Note:
calculation is based on composition analysis of the organic phase from the 1st extraction.

B: Extraction of $CaBr_2$ from $CaBr_2$-Glucose Solution with n-Butanol

As mentioned above, $CaBr_2$ can work as effectively as LiBr to hydrolyze lignocellulosic biomass. $CaBr_2$ was extracted from glucose with the butanol extraction method as described above (A). Results indicated that $CaBr_2$ could also be extracted into butanol/hexane, and that a lower butanol/hexane ratio (5:5) facilitated the separation of $CaBr_2$ and glucose. When extracting $CaBr_2$-glucose solution (1500 mg $CaBr_2$, 1 mL water, 200 mg glucose) with butanol/hexane (7:3), only approximately 95 mg glucose was left in the aqueous phase after 10 extractions. More than half of the initial glucose was extracted to the solvent phase. When butanol/hexane ratio was reduced to 5:5, extracting the same $CaBr_2$-glucose solution (1500 mg $CaBr_2$, 1 mL water, 200 mg glucose) 30 times decreased $CaBr_2$ from 1500 mg to 70 mg, but glucose only decreased from 200 mg to 190 mg. Only 10 mg glucose was extracted into 5:5 butanol/hexane. It was noted that more extractions were needed to extract $CaBr_2$ than LiBr.

C: Extraction of LiBr from Biomass Hydrolysate with n-Butanol

LiBr from biomass hydrolysate was extracted using n-butanol. Spruce powder (4 g) was hydrolyzed using the conditions of entry 4 in Table 6. After the hydrolysis, the hydrolysate was centrifuged to separate supernatant and precipitate (lignin and unhydrolyzed spruce, if any). Precipitate was washed with 5 mL n-butanol (2×) to recover LiBr in the precipitate. The butanol washings were mixed with hexane to a butanol/hexane ratio of 7:3 (v/v) and used as extraction solvent. The collected supernatant (containing 0.048 g Arabinose, 0.084 Arabinose, 1.64 g glucose, 0.2 g Xylose, 0.4 g Mannose and LiBr) was extracted with butanol/hexane (7:3) (20 extractions) in a 50-mL screw capped bottle. Specifically, 5 mL organic solvent was used in the first extraction. After vortexing for 1 min, the bottle was centrifuged to separate organic phase and aqueous phase. When the organic phase was removed, 5 mL fresh organic solvent was added. The extraction was repeated 20 times. After the extractions, the resulting syrup-like sugar mixture was analyzed, and found to contain 1.4 g glucose, 0.075 g xylose, 0.3 g mannose, 0.260 g LiBr, and 1 mL water. From the sugar content of spruce shown in Table 6 and initial LiBr concentration, the recovery yields of glucose, xylose and mannose were calculated to be 83, 36, and 74%, respectively. Additionally 96.5% of initially loaded LiBr was recovered. Unrecovered sugars were found to be accounted for in the small amount of the sugars degraded to furfural and HMF during the hydrolysis, with the remainder extracted into the organic layer. Any sugars extracted into the organic layer can be recycled.

Example 16

Removal of Residual Low-Concentration LiBr from Sugar Stream by Precipitation of Sugars with Anti-Solvent Because sugars have lower solubility in organic solvent than in water, if a water-miscible anti-solvent such as methanol, ethanol or acetone, in which sugars are insoluble and LiBr is soluble, is added to the sugar-LiBr mixture, the sugars will precipitate, and LiBr will retain in the mother liquor. Using this precipitation method, sugars and LiBr should be completely separated.

However, it was found that the direct addition of methanol or ethanol did not work to precipitate sugars. It was found that the alcohols and the syrup were miscible. This may be due to the presence of water and LiBr in the syrup, which increased the solubility of sugars in the water-alcohol mixture. Addition of lower-polarity acetone into the syrup also did not work to precipitate sugars. Acetone partially dissolved the sugar syrup, and the undissolved portion still contained a significant amount of LiBr. This indicated that acetone is unable to extract LiBr and precipitate pure sugars. The dissolution of sugars in organic solvent is attributed to the presence of water in the solvent In order to reduce the dissolution of sugars in organic solvent, water was removed by evaporation before the precipitation step. The presence of LiBr was found to make the complete removal of water in the sugar syrup through vaporization very difficult, because of the extremely low vapor pressure of LiBr-water. It was found that when the water was evaporated, the syrup was still soluble in methanol, but became partially soluble in ethanol, and insoluble in acetone. From these observations, if the syrup is first dissolved into methanol or ethanol and the resulting solution poured into acetone, sugars are expected to precipitate out with LiBr remaining in the solution. Pure glucose syrup with very small amount of water was first tested. For example, 320 mg glucose, 50 mg LiBr, and 50 µL water were dissolved in 1 mL methanol at 80° C. The resulting solution was then added into 10 mL acetone dropwise with stirring. It turned out that glucose precipitated and could be separated by centrifugation. The results showed that 240 mg glucose (75%) was recovered as a solid, and only 4.5 mg LiBr (9%) carried over into the solid.

A sugar syrup prepared from spruce hydrolysis was tested with this method. The sugar syrup (containing glucose: ~280 mg; xylose: ~15 mg; mannose: ~60 mg; LiBr: 50 mg; and water: 0.2 mL) was first evaporated to reduce the water content from 0.2 mL to 0.05 mL. The concentrated syrup was dissolved in 1 mL methanol at 80° C. This solution was then added into 10 mL acetone dropwise with vigorous stirring to allow the formation of sugar precipitate. The sugar precipitate was collected, and LiBr left in the solution. Approximately 220 mg glucose and 4 mg LiBr were found in the precipitate. In other words, 79% of the glucose of the syrup was recovered and only 8% LiBr of the syrup was carried over with the sugar. The results were comparable with those from glucose and LiBr above.

In summary, dissolving a sugar-LiBr mixture in methanol and then adding the solution to acetone can precipitate sugars. This method can avoid the strong interaction among the sugars, water, and LiBr. Addition of methanol weakened the interaction of LiBr, sugar, and water and increased the solubility of LiBr in acetone. Most of the LiBr salt was dissolved into acetone and most of the sugars were precipitated out. However, small amounts of glucose and xylose were dissolved into organic solvent as well with LiBr, requiring further separation. In addition, a large amount of acetone was needed to precipitate sugars in this method. However, dissolved sugar and LiBr in organic solvent can be readily recycled together and separated in the next cycle.

Example 17

Removal of Residual Low-Concentration LiBr from Sugar Stream by Crystallization of Sugars in Anti-Solvent Removing water from the sugar syrup by vaporizing the water significantly decreased the solubility of sugar in ethanol. When the syrup was dissolved in ethanol at elevated temperature, ethanol broke the strong interactions between sugars, water, and LiBr. Because of the high solubility of LiBr and low solubility of glucose in ethanol, glucose is expected to crystallize when the solution is cooled down.

Glucose was dissolved in ethanol by heating to 120° C. to facilitate dissolution. The resulting clear solution was then cooled to room temperature with stirring to allow sugar crystallization (or precipitation). Precipitated glucose was filtered and washed with ethanol. However, a small amount of glucose was found dissolved in ethanol, and therefore glucose was not fully recovered. The effect of LiBr and water on the precipitation of glucose in ethanol was investigated, and the results are shown in Table 16.

TABLE 16

Effects of LiBr and water on the precipitation of glucose by ethanol

| Entry | LiBr, mg | Water, µL | Precipitated glucose, mg |
|---|---|---|---|
| 0 | 0 | 0 | 400 |
| 1 | 50 | 30 | 330 |
| 2 | 50 | 50 | 330 |
| 3 | 50 | 100 | 330 |
| 4 | 50 | 150 | 330 |
| 5 | 100 | 150 | 320 |
| 6 | 150 | 150 | 300 |
| 7 | 200 | 150 | 250 |

Note:
Certain amount of LiBr and water (as shown in the Table), 400 mg glucose, and 2 mL ethanol were mixed and heated to 120° C. under stirring until a clear solution formed. Then solution was cooled down to room temperature naturally under stirring and stirred for additional 20 min. Sugar precipitated out and was filtrated and then washed with 5 ml ethanol. The precipitate then was dried at 105° C.

A sample of the sugar syrup from spruce hydrolysis (after butanol extraction) contained glucose: ~280 mg; xylose: ~15 mg; mannose: ~60 mg, LiBr: 50 mg, water: 0.2 mL. The sample was vaporized to reduce water content from 0.2 mL to 0.05 mL. The same crystallization operation was carried out as for pure glucose above. It was found that approximately 200 mg glucose was precipitated and recovered. Almost all other sugars and LiBr were however retained in the ethanol. It was also found that hemicellulose sugars such as xylose were very difficult to crystallize. In addition, xylose may negatively affect the crystallization of glucose.

In summary, precipitation or crystallization in anti-solvent was not found to be an efficient way to completely separate sugars and LiBr. Some sugars, in particular hemicellulose sugars could not be effectively recovered using this method.

Example 18

Removal of Residual Low-Concentration LiBr from Sugar Stream by Ion Exchange Chromatography Although sugars and LiBr could be separated by ion exclusion chromatography, as discussed in Example 10, recovered LiBr and sugars were extremely diluted (both at concentration of ~1%). It is energy-intensive to reconcentrate materials for recycling or downstream processing. The ion exclusion method may thus be not feasible in industrial application.

To keep the sugar concentration as high as possible, ion exchange chromatography is an alternative method to remove residual LiBr from concentrated sugar syrup. Ion exchange resin has been widely used to remove salt by exchanging the cation and anion in salt with $H^+$ and $OH^-$ ions on the resin. The disadvantage of ion exchange resin is that when $H^+$ and $OH^-$ ions are consumed, the resin needs to be regenerated by flushing with acid (cation exchange resin) or with alkali (anion exchange resin). Direct application of ion exchange resin to concentrated hydrolysate without pre-removal of LiBr by butanol extraction is not feasible. The high concentration of LiBr would require the use of large amounts of ion exchange resin and regeneration of the spent resins would consume large amounts of acid and alkali. However, when the majority of LiBr is first removed by solvent extraction, such as the butanol extraction in Example 11, it is feasible to remove the remaining salt using ion exchange resin.

(1) Removal of LiBr $Resin-H^+ + LiBr \rightarrow Resin-Li^+ + HBr$ $Resin-OH^- + HBr \rightarrow Resin-Br^- + H_2O$ (2) Regeneration of Resins $Resin-Li^+ + \frac{1}{2}H_2SO_4 \rightarrow Resin-H^+ + \frac{1}{2}Li_2SO_4$ $Resin-Br^- + \frac{1}{2}Ca(OH)_2 \rightarrow Resin-OH^- + \frac{1}{2}CaBr_2$ (3) Recovery of Residual LiBr $\frac{1}{2}Li_2SO_4 + \frac{1}{2}CaBr_2 \rightarrow LiBr + \frac{1}{2}CaSO_4\downarrow$ The consumption of the acid and alkali for resin regeneration is estimated to be comparable to that for neutralizing the acid used in the diluted acid hydrolysis of biomass. Typically, 1~5% acid loading (on biomass) is required in diluted acid hydrolysis or pretreatment of biomass. Residual acid is typically neutralized with calcium hydroxide, and gypsum forms.

After the spruce hydrolysate was extracted with butanol/hexane, the concentration of resulting sugar syrup reached 67% solid content (1.4 g glucose, 0.075 g xylose, 0.3 g mannose, 0.260 g LiBr in 1 mL water). The syrup was first diluted to ~50% solid with water before loading onto the ion exchange columns. Two small columns (1 cm in diameter and 5 cm in length) were packed with anion exchange resin (DOWEX-2, $Cl^-$ form, 100~200 mesh) and cation exchange resin (Amberlyst 15, 25~50 mesh), respectively. Prior to operation, the anion exchange column was washed with 10 mL 5% sodium hydroxide solution, and cation exchange column was washed with 10 mL 5% sulfuric acid. The columns were then washed with water until neutral pH. Both columns were de-watered by injecting air to prevent the water from diluting the sugar solution. The diluted syrup of 0.5 mL was loaded onto the cation exchange column first to remove $Li^+$. The loaded sample was pushed through the column by injecting air. The recovered solution was then loaded onto the anion exchange column to remove $Br^-$. Again, air was used to push the sample through the column. The recovered solution was analyzed for LiBr. The results indicated that LiBr was completely removed. The concentration of the sugars was unchanged because no dilution occurred. Certainly, one can pass the syrup through the anion column first followed by the cation column. In industrial operation, the two columns can be installed in series and sugar syrup can be applied continuously to the columns in series. Since the sugar syrup will be injected continuously to the columns, no air is needed to push the syrup through the columns.

Example 19

Removal of Residual Low-Concentration LiBr from Sugar Stream by Precipitation with Sodium Carbonate Another method to remove LiBr from sugar stream is the precipitation method with sodium carbonate. This is can be an effective way to remove small amounts of LiBr in the sugar stream after the majority of LiBr is extracted with butanol and hexane. Sodium carbonate reacts with LiBr to form lithium carbonate precipitate according to the following reaction.

$2LiBr + Na_2CO_3 \rightarrow Li_2CO_3\downarrow + 2NaBr$

Since lithium carbonate is insoluble in water, it can be readily separated from aqueous solution by filtration or centrifugation. For reuse, the recovered lithium carbonate can be converted back to lithium bromide according to the reaction:

$Li_2CO_3 + 2HBr \rightarrow 2LiBr + H_2O + CO_2\uparrow$

Example 20

Integrated Methods to Separate LiBr from Sugar Stream

Figure 7:
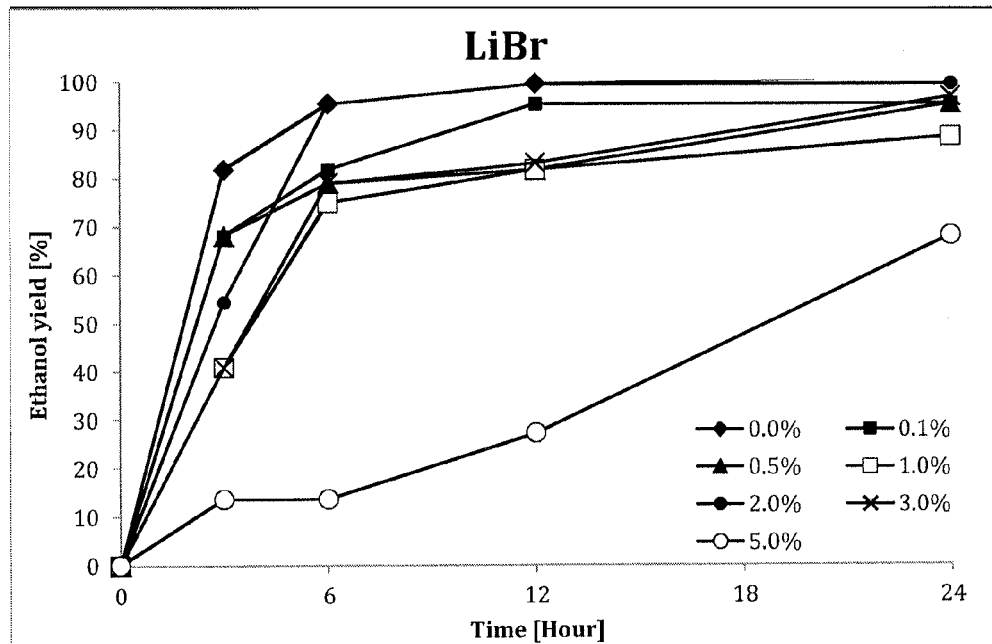
FIG. 7 is a graph showing glucose fermentation by *S. cerevisiae* in the presence of LiBr at concentrations ranging from 0 to 5% (w/v).

Though all the methods discussed above (Examples 9-15) can be used to separate LiBr and sugars, none of them can completely separate the salt and sugars in an effective and economic way. Combination of different methods is, however a feasible way for complete separation of LiBr and sugars. A preferable combination is shown in FIG. 7. Extraction with butanol or mixtures of butanol/hexane is used first to remove most of LiBr from sugars, and then the residual small amount of LiBr is removed either by ion exchange columns or by precipitation with sodium carbonate.

Example 21

Fermentation of Sugars in the Presence of Residual LiBr or $CaBr_2$

Complete separation of LiBr from sugars is difficult and expensive. Small amounts of LiBr or $CaBr_2$ may be retained in the sugar product stream generated by the processes of this invention. If the sugars are intended for use for fermentation, the residual salt could potentially affect the fermentation. To investigate whether residual LiBr or $CaBr_2$ inhibits fermentation, glucose was fermented to ethanol with the yeast *Saccharomyces cerevisiae* in the presence of varied concentrations of LiBr or $CaBr_2$.

Figure 8:
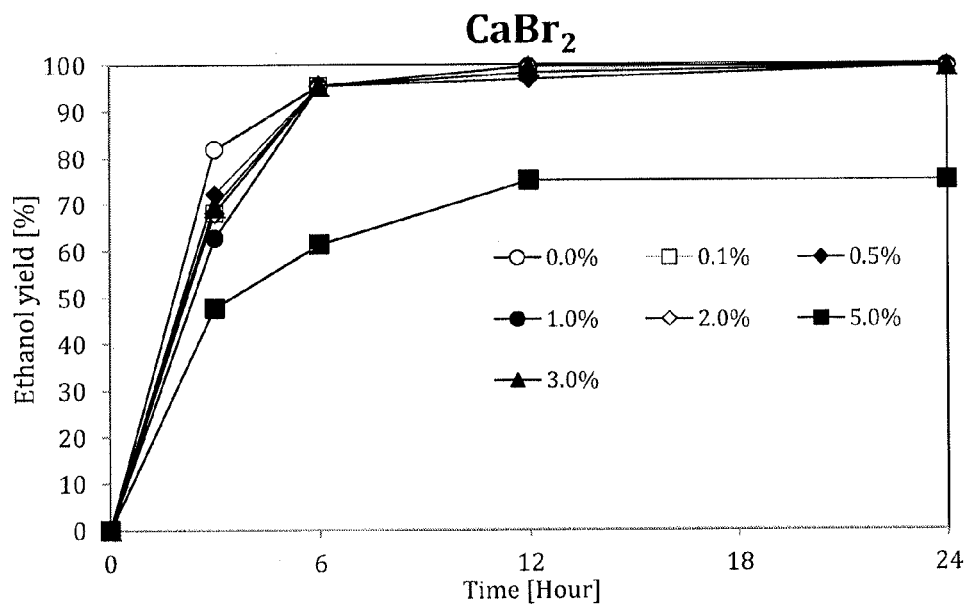
FIG. 8 is a graph showing glucose fermentation by *S. cerevisiae* in the presence of CaBr2 at salt concentrations ranging from 0 to 5% (w/v).
Figure 9A:
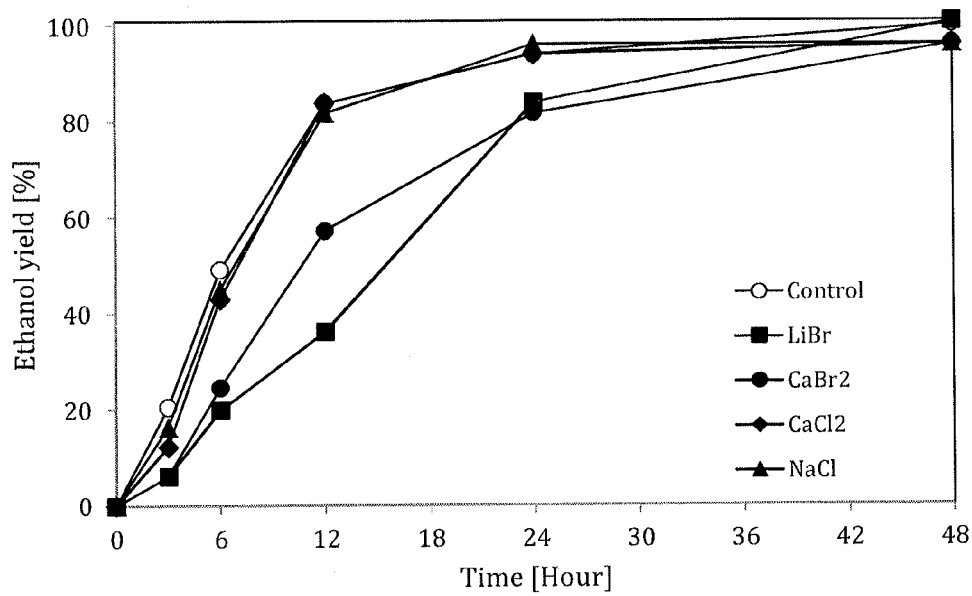
FIGS. 9A and 9B are graphs providing a comparison of the inhibition of glucose fermentation by *S. cerevisiae* by different salts at 2% (w/v) salt (FIG. 9A) and 5% (w/v) salt (FIG. 9B).
Figure 9B:
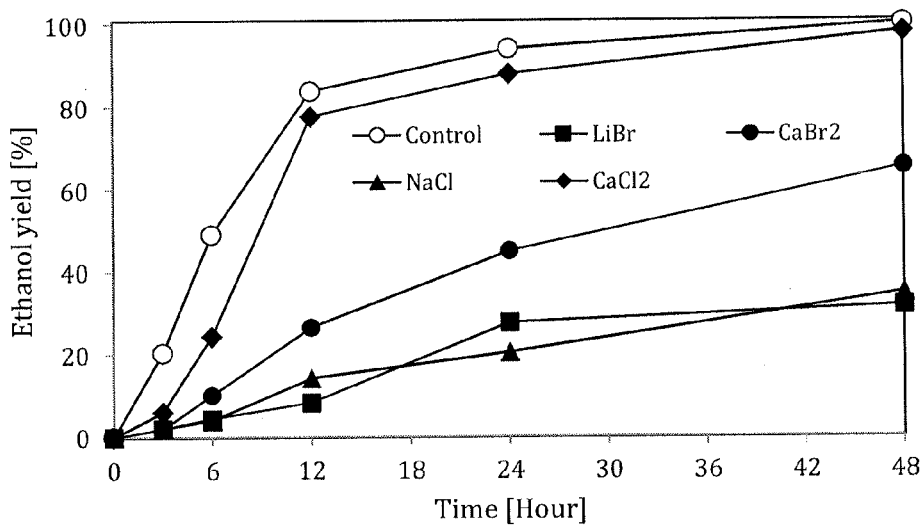

The results are shown in FIGS. 7, 8 and 9A-B. As shown in FIG. 7, LiBr concentration was below 5% (w/v), LiBr did not have significant inhibition on sugar fermentation. However, when LiBr concentration reached 5% (w/v), the inhibition was significant. As shown in FIG. 8, CaBr2 was generally less inhibitory to fermentation and ethanol yield was higher. Inhibition became more significant at a $CaBr_2$ concentration of 5% (w/v).

These results indicate that residual LiBr and $CaBr_2$ at levels below about 5% (w/v) can be tolerated in sugar product streams intended for use in fermentation to produce ethanol.

The inhibitor effect on fermentation by LiBr and $CaBr_2$ was compared to that of related salts NaCl and $CaCl_2$ at 2% (w/v) and 5% (w/v) of salt. At the lower salt concentration (2%, FIG. 9A), LiBr and $CaBr_2$ were more inhibitory than NaCl and $CaCl_2$. However, at 5% concentration (FIG. 9B), NaCl showed inhibition similar to LiBr. $CaCl_2$ does not appear to be inhibitory to sugar fermentation at the investigated concentrations.

REFERENCES

[1] A. M. Smith, *Plant J* 2008, 54, 546-558.
[2] A. Demirbas, *Energ Source* 2005, 27, 327-337.
[3] a S. Miller, R. Hester, *Chem Eng Commun* 2007, 194, 85-102; b Z. G. Zhu, N. Sathitsuksanoh, T. Vinzant, D. J. Schell, J. D. McMillan, Y. H. P. Zhang, *Biotechnol Bioeng* 2009, 103, 715-724.
[4] a J. Lawrence J. Russo, Vol. U.S. Pat. No. 5,968,362, 1999; b W. A. F. a. J. Cuzens, Vol. U.S. Pat. No. 5,820,687, 1998.
[5] a J. F. Harris, Forest Products Laboratory (U.S.), *Two-stage, dilute sulfuric acid hydrolysis of wood: an investigation of fundamentals*, U.S. Dept. of Agriculture, Forest Service, Forest Products Laboratory, [Madison, Wis.], 1985; b J. I. Zerbe, A. J. Baker, Forest Products Laboratory (U.S.), *Investigation of fundamentals of two-stage, dilute sulfuric acid hydrolysis of wood*, Forest Products Laboratory, [Madison, Wis.?, 1988.
[6] a Y. H. P. Zhang, M. E. Himmel, J. R. Mielenz, *Biotechnology Advances* 2006, 24, 452-481; b R. K. Sukumaran, R. R. Singhania, A. Pandey, *Journal of Scientific & Industrial Research* 2005, 64, 832-844.
[7] a Y. Yang, R. Sharma-Shivappa, J. C. Burns, J. J. Cheng, *Energ Fuel* 2009, 23, 3759-3766; b X. Pan, D. Xie, K. Y. Kang, S. L. Yoon, J. N. Saddler, *Appl Biochem Biotechnol* 2007, 137-140, 367-377; c V. Balan, B. Bals, S. P. Chundawat, D. Marshall, B. E. Dale, *Methods Mol Biol* 2009, 581, 61-77; d A. P. Dadi, S. Varanasi, C. A. Schall, *Biotechnology and Bioengineering* 2006, 95, 904-910; e N. Sathitsuksanoh, Z. Zhu, T. J. Ho, M. D. Bai, Y. H. Zhang, *Bioresour Technol* 2010, 101, 4926-4929; f S. McIntosh, T. Vancov, *Bioresour Technol* 2010, 101, 6718-6727; g B. Yang, C. E. Wyman, *Biofuels Bioproducts & Biorefining-Biofpr* 2008, 2, 26-40; h C. E. Wyman, B. E. Dale, R. T. Elander, M. Holtzapple, M. R. Ladisch, Y. Y. Lee, *Bioresource Technology* 2005, 96, 1959-1966; i N. Mosier, C. Wyman, B. Dale, R. Elander, Y. Y. Lee, M. Holtzapple, M. Ladisch, *Bioresource Technology* 2005, 96, 673-686.
[8] a C. Z. Li, Q. Wang, Z. K. Zhao, *Green Chem* 2008, 10, 177-182; b C. Z. Li, Z. K. B. Zhao, *Advanced Synthesis & Catalysis* 2007, 349, 1847-1850; c J. B. Binder, R. T. Raines, *Proc Natl Acad Sci USA* 2010, 107, 4516-4521.
[9] B. M. Holmes, T. C. R. Brennan, S. Datta, H. W. Blanch, B. A. Simmons, *Bioenerg Res* 2010, 3, 123-133.
[10] a R. T. Nagle, Power Alcohol, Inc., U.S., 1987; b R. T. Nagle, Power Alcohol, Inc., U.S., 1987; c R. A. Penque, Vol. U.S. Pat. No. 4,018,620, 1977; d L. Y. Chen, Cheming, Vol. U.S. Pat. No. 4,452,640, 1984.
[11] a S. Fischer, H. Leipner, K. Thummler, E. Brendler, J. Peters, *Cellulose* 2003, 10, 227-236; b N. J. Cao, Q. Xu, C. S. Chen, C. S. Gong, L. F. Chen, *Applied Biochemistry and Biotechnology* 1994, 45-6, 521-530.
[12] M. H. B. Wolfram Rudolph, and Cory C. Pye, *J. Phys. Chem.* 1995, 99, 3793-3797.
[13] s. F. a. H. L. Erica Brendler, *cellulose* 2002, 8, 283-288.
[14] C. K. Dian Jiao, Alan Grossfield, Thomas A. Darden, and Pengyu Ren, *J. Phys. Chem. B* 2006, 110, 18553-18559.
[15] a T. H. T. Ting Chia Huang, *J. Chem. Eng. Data* 1991, 36, 231-235; b G. z. a. Z. Shenlin, *Chinese Journal of Chemical Engineering* 1998, 6, 124-129.
[16] H. B. a. E. Uhlemanna, *Separation Science and Technology* 1993, 28, 1357-1360.
[17] B. Grinbaum, L. Kogan, E. Barnea, G. Harel, R. Semiat, S. Wahrmann, U.S. Pat. No. 7,452,520, 2008.
[18] J. A. Duffy and M. D. Ingram. 1978. Acidic nature of metal aquo complexes: proton-transfer equilibria in concentrated aqueous media. Inorganic Chemistry, 17 (10), 2798-2802.
[19] G. E. P. Box and N. R. Draper. 2007. Response Surfaces, Mixtures, and Ridge Analyses, Second Edition, Wiley.

The invention claimed is:

1. A method for solubilizing and/or hydrolyzing lignocellulosic material which comprises the step of contacting the lignocellulosic material with an aqueous solution of a bromine salt at temperatures ranging from 100-160°C., wherein the bromine salt at temperatures ranging from 100-160° C. is present in the solution at a concentration of 40-80% by weight of the solution.

2. The method of claim 1 wherein the aqueous solution further comprises acid at a concentration of 1M or less.

3. The method of claim 2 wherein the acid concentration is less than 0.5M.

4. The method of claim 2 wherein the acid is an inorganic acid.

5. The method of claim 2 wherein the acid is HCl or $H_2SO_4$.

6. The method of claim 1 wherein the bromine salt is LiBr or $CaBr_2$.

7. The method of claim 6 wherein the concentration of bromine salt ranges from 55 to 65% by weight.

8. The method of claim 1 wherein the temperatures range from 100 to 130° C.

9. The method of claim 1 wherein the volume:weight ratio of solution to lignocellulosic material ranges from 10:1 to 1:1.

10. A method for obtaining sugars from lignocellulosic materials which comprises the steps of solubilizing and/or hydrolyzing lignocellulosic material by a method of claim 1 to obtain a salt-sugar product mixture and separating the salt from the sugar to obtain a sugar product containing less than 10% by weight of the salt.

11. The method of claim 10 wherein the sugar product obtained contains less than 1% by weight of the salt.

12. The method of claim 10 wherein the salt is extracted from the salt-sugar product mixture by extraction with an organic phase in which the sugar is not soluble.

13. The method of claim 12 wherein the organic phase used for extraction is butanol or a mixture of butanol and hexane.

14. The method of claim 12 wherein the salt-sugar product is extracted a plurality of times with the organic phase in a continuous, semi-continuous, or batch extraction.

15. The method of claim 12 wherein residual salt is removed from the extracted sugar by ion exchange chromatography, ion exclusion chromatography, crystallization or precipitation.

16. The method of claim 15 wherein sequential steps of anion and cation exchange are applied to remove residual salt.

17. The method of claim 15 wherein residual salt is removed by precipitation with a carbonate salt.

18. A method for production of ethanol by fermentation which employs a hydrolysis product made by the method of claim 1 as a feedstock.

19. The method of claim 18 wherein the hydrolysis product contains less than 5% by weight of HMF and furfural.

20. The method of claim 18 wherein the hydrolysis product contains less than 5% by weight of bromine salt.

* * * * *